United States Patent [19]
Warpehoski et al.

[11] Patent Number: 5,847,153
[45] Date of Patent: Dec. 8, 1998

[54] β-SULFONYL HYDROXAMIC ACIDS

[75] Inventors: Martha A. Warpehoski, Portage; Donald E. Harper, Plainwell, both of Mich.

[73] Assignee: Pharmacia & Upjohn Company, Kalamazoo, Mich.

[21] Appl. No.: 934,408

[22] Filed: Sep. 19, 1997

Related U.S. Application Data

[60] Provisional application No. 60/026,848, Sep. 27, 1996.

[51] Int. Cl.$^6$ .................................................. C07D 233/40
[52] U.S. Cl. ........................................ 548/319.5; 562/621
[58] Field of Search ......................... 562/621; 548/319.5

[56] References Cited

U.S. PATENT DOCUMENTS

| | | | |
|---|---|---|---|
| 5,240,958 | 8/1993 | Campion et al. | 514/445 |
| 5,525,629 | 6/1996 | Crimmin et al. | 514/542 |
| 5,691,382 | 11/1997 | Crimmin et al. | 514/575 |

FOREIGN PATENT DOCUMENTS

| | | | |
|---|---|---|---|
| 0640 594 A | 1/1995 | European Pat. Off. | C07D 233/72 |
| 0780 386 | 6/1997 | European Pat. Off. | C07D 309/08 |
| WO 90/05719 | 5/1990 | WIPO | C07C 323/62 |
| WO 93/20047 | 10/1993 | WIPO | C07C 317/44 |
| WO 95/09841 | 4/1995 | WIPO | C07C 323/60 |
| WO 97/24117 | 7/1997 | WIPO | A61K 31/19 |

OTHER PUBLICATIONS

Database CAPLUS, No. 125:266005, Hodgkin et al., 'Use of matrix metalloproteinase inhibitors for treatment of diseases mediated by TGF–alpha.' abstract of WO 9625156 A1, Aug. 22, 1996.

Database CAPLUS, No. 128:75188, Takahashi et al., Preparation and formulation of aryl sulfides, sulfoxides, and sulfones as matrix metalloproteinase inhibitors.' abstract of WO 9749679 A1, Dec. 13, 1997.

*Primary Examiner*—Gary Geist
*Assistant Examiner*—Brian J. Davis
*Attorney, Agent, or Firm*—Lucy X. Yang

[57] ABSTRACT

The present invention provides a compound of formula I

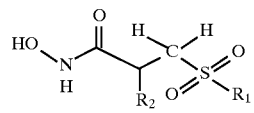

or pharmaceutical acceptable salts thereof wherein $R_1$ is $C_{4-12}$ alkyl, $C_{4-12}$ alkenyl, $C_{4-12}$ alkynyl, —$(CH_2)_h$-$C_{3-8}$ cycloalkyl, —$(CH_2)_h$-aryl, or —$(CH_2)_h$-het; $R_2$ is $C_{1-12}$ alkyl, $C_{2-12}$ alkenyl, $C_{2-12}$ alkynyl, —$(CH_2)_h$-$C_{3-8}$ cycloalkyl, —$(CH_2)_h$-$C_{3-8}$ cycloalkenyl, —$(CH_2)_h$-aryl, —$(CH_2)_h$-het, —$(CH_2)_h$-Q, —$(CH_2)_i$-X-$R_4$, or —$(CH_2)_i$CHR$_5$R$_6$. The compounds are inhibitors of matrix metalloproteinases involved in tissue degradation.

18 Claims, No Drawings

β-SULFONYL HYDROXAMIC ACIDS

CROSS-REFERENCE TO RELATED APPLICATION

This application claims the benefit of the following provisional application: U.S. Ser. No. 60/026,848, filed Sep. 27, 1996, under 35 USC 119(e)(i).

FIELD OF THE INVENTION

The present invention relates to novel β-sulfonyl hydroxamic acids, to pharmaceutical compositions containing them, and to the method of using them. The compounds of the invention are inhibitors of matrix metalloproteinases involved in tissue degradation.

BACKGROUND OF THE INVENTION

Loss of connective tissue integrity occurs in many disease processes, including osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, inflammation, asthma and other diseases related to connective tissue degradation. Although there is a high incidence of these diseases in the developed world, there is no treatment that prevents the tissue damage that occurs. Considerable lines of scientific evidence indicate that uncontrolled connective matrix metalloproteinase (MMPs) activity is responsible for the damage, and as a consequence the inhibition of these enzymes has become the target for therapeutic intervention (see Matrisian, L. M., Bases, Vol. 14, pp 445–463 (1992); Emonard, H. et al., Cellular and molecular Biology, Vol. 36, pp 131–153 (1990); Docherty, A. J. P. et al., Annals of the Rheumatic, Vol. 49, pp 469–479 (1990)).

Hydroxamic acid derivatives are a class of known therapeutically active MMPs inhibitors and there are numerous references in the art disclosing a variety of hydroxamic acid derivatives. For example, European Patent Publication 0,606,046 A1 discloses arylsulfonamido-substituted hydroxamic acids useful as matrix metalloproteinase inhibitors. International Publication Nos. WO 95/35275 and WO 95/35276 disclose sulfonamide hydroxamic acid and carboxylic acid derivatives useful as matrix metalloproteinases inhibitors. All these references relate to sulfonamide hydroxamic acids. The compounds of this invention are novel and distinct from all other sulfonamide hydroxamic acids in that the usual nitrogen atom is replaced by a carbon atom. The invention provides sulfonyl hydroxamic acid derivatives.

The compounds of the present invention inhibit various enzymes from the matrix metalloproteinase family, predominantly stromelysin and gelatinase, and hence are useful for the treatment of matrix metallo endoproteinase diseases such as osteoporosis, tumor metastasis (invasion and growth), periodontitis, gingivitis, corneal ulceration, dermal ulceration, gastric ulceration, inflammation, asthma, and other diseases related to connective tissue degradation.

INFORMATION DISCLOSURE

The following references disclose sulfonyl hydroxamic acid derivatives.

International Publication No. WO 95/09841 discloses hydroxamic acid compounds useful as inhibitors TNF and matrix metalloproteinases.

International Publication No. WO 93/20047 discloses hydroxamic acid compounds useful as inhibitors of tumour necrosis factor production and of matrix metalloproteinases.

International Publication No. WO 90/05719 discloses hydroxamic acid compounds useful in the management of diseases involving tissue degradation and/or the promotion of wound healing.

The hydroxamic acid compounds in the above identified references have an obligatory peptide backbone. The compounds of the present invention are distinct from the above noted references in that they do not have a peptide backbone.

The European Patent Application EP 0780 386 A1 discloses matrix metalloproteinases inhibitors useful in the treatment of mammals having disease states alleviated by the inhibition of such matrix metalloproteinases.

International Publication No. WO 97/24117 discloses substituted aryl, heteroaryl, arylmethyl or heteroarylmethyl hydroxamic acid compounds especially useful for inhibiting the production or physiological effects of TNF in the treatment of a patient suffering from a disease state associated with a physiologically detrimental excess of tumor necrosis factor (TNF).

SUMMARY OF THE INVENTION

The present invention provides novel compounds of formula I

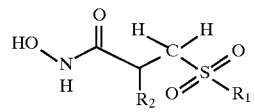

or pharmaceutical acceptable salts thereof wherein:

$R_1$ is
- a) $C_{4-12}$ alkyl,
- b) $C_{4-12}$ alkenyl,
- c) $C_{4-12}$ alkynyl,
- d) —$(CH_2)_n$-$C_{3-8}$ cycloalkyl,
- e) —$(CH_2)_n$-aryl,
- f) —$(CH_2)_n$-aryl substituted with $C_{1-4}$ alkyl, $C_{1-4}$ alkoxy, halo, —$NO_2$, —$CF_3$, —CN, or —$N(C_{1-4}$ alkyl$)_2$,
- g) —$(CH_2)_n$-het, or
- h) —$(CH_2)_n$-het substituted with $C_{1-4}$ alkyl, or halo;

$R_2$ is
- a) $C_{1-12}$ alkyl,
- b) $C_{1-12}$ alkyl substituted with one to three halo, —CN, —$NO_2$, —$CF_3$, —$N(R_3)_2$, —$SR_3$, or OH,
- c) $C_{2-12}$ alkenyl,
- d) $C_{2-12}$ alkenyl substituted with one to three halo, —CN, —$NO_2$, or —$CF_3$,
- e) $C_{2-12}$ alkynyl,
- f) $C_{2-12}$ alkynyl substituted with one to three halo, —CN, —$NO_2$, or —$CF_3$,
- g) —$(CH_2)_n$-$C_{3-8}$ cycloalkyl,
- h) —$(CH_2)_n$-$C_{3-8}$ cycloalkyl substituted with one to three $C_{1-4}$ alkyl, $C_{1-4}$ alkoxy, or halo,
- i) —$(CH_2)_n$-$C_{3-8}$ cycloalkenyl,
- j) —$(CH_2)_n$-$C_{3-8}$ cycloalkenyl substituted with one to three $C_{1-4}$ alkyl, $C_{1-4}$ alkoxy, or halo,
- k) —$(CH_2)_n$-aryl,
- l) —$(CH_2)_n$-aryl substituted with one to three $C_{1-4}$ alkyl, $C_{1-4}$ alkoxy, —$CF_3$—OH, —$NO_2$, —CN, —$N(R_3)_2$, —$SR_3$,—$SO_2(C_{1-4}$ alkoxy),—C(=O)$R_3$, or —NC(=O)$R_3$,
- m) —$(CH_2)_n$-aryl substituted with one to five halo,
- n) —$(CH_2)_n$-het,
- o) —$(CH_2)_n$-het substituted with one to two $C_{1-4}$ alkyl, or halo, p) —$(CH_2)_h$-Q,
q) —$(CH_2)_h$-Q substituted with one to three $C_{1-4}$ alkyl, $C_{1-4}$ alkoxy, halo, or phenyl,
r) —$(CH_2)_i$-X-$R_4$, optionally the $(CH_2)_i$- chain can be substituted with $C_{1-4}$ alkyl or phenyl, which in turn can be substituted with one to three halo or $C_{1-4}$ alkyl, or
s) —$(CH_2)_i CHR_5 R_6$;

$R_3$ is
a) H,
b) $C_{1-4}$ alkyl,
c) —$(CH_2)_h$-phenyl, or
d) —$(CH_2)_h$-phenyl substituted with one to three $C_{1-4}$ alkyl, $C_{1-4}$ alkoxy, or halo;

X is
a) —O—,
b) —S(=O)$_j$-,
c) —$NR_7$-,
d) —S(=O)$_2 NR_8$-, or
e) —C(=O)—;

$R_4$ is
a) H,
b) $C_{1-4}$ alkyl,
c) —$(CH_2)_h$-phenyl,
d) —$(CH_2)_h$-phenyl substituted with one to three $C_{1-4}$ alkyl, $C_{1-4}$ alkoxy, halo, —$NO_2$, or —CN, or
e) —$(CH_2)_h$-het;

$R_5$ is
a) $C_{1-4}$ alkyl, or
b) —C(=O)$R_3$;

$R_6$ is
a) —C(=O)$R_3$, or
b) —$(CH_2)_h$C(=O)$R_3$;

$R_7$ is
a) H,
b) $C_{1-4}$ alkyl,
c) —$(CH_2)_h$-phenyl,
d) —$(CH_2)_h$-phenyl substituted with one to three $C_{1-4}$ alkyl, $C_{1-4}$ alkoxy, or halo,
e) —C(=O)—$R_3$,
f) —S(=O)$_2 R_3$, or
g) —C(=O)O$R_3$;

$R_8$ is
a) $C_{1-4}$ alkyl,
b) —$(CH_2)_h$-phenyl, or
c) —$(CH_2)_h$-phenyl substituted with one to three $C_{1-4}$ alkyl, $C_{1-4}$ alkoxy, or halo;

aryl is monocarbocyclic, or bicarbocyclic aromatic moiety;

het is 5- to 10-membered unsaturated heterocyclic moiety having one to three atoms selected from the group consisting of oxygen, nitrogen, and sulfur;

Q is 5- to 10-membered saturated heterocyclic moiety having one to two atoms selected from the group consisting of oxygen, nitrogen, and sulfur;

h is 0, 1, 2, 3, 4, 5, or 6; i is 0, 1, 2, 3, 4, 5, 6, 7, 8, 9, or 10; and j is 0, 1, or 2.

The compounds of the present invention inhibit various enzymes from the matrix metalloproteinase family, predominantly stromelysin and gelatinase, and hence are useful for the treatment of matrix metallo endoproteinase diseases

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive. Thus, $C_{1-4}$ alkyl refers to alkyl of one to four carbon atoms, inclusive, or methyl, ethyl, propyl, butyl and isomeric forms thereof.

The terms "$C_{1-4}$ alkyl", "$C_{4-8}$ alkyl", "$C_{1-12}$ alkyl", and "$C_{1-18}$ alkyl" refer to an alkyl group having one to four, four to eight, one to twelve, or one to eighteen carbon atoms respectively such as; for example, methyl, ethyl, propyl, butyl, pentyl, hexyl, heptyl, octyl, nonyl, decyl, undecyl, dodecyl, tridecyl, tetradecyl and their isomeric forms thereof, preferably an alkyl group of $R_1$ having four to eight carbon atoms, and an alkyl group of $R_2$ having one to eight carbon atoms.

The terms "$C_{2-12}$ alkenyl" and "$C_{4-8}$ alkenyl" refer to at least one double bond alkenyl group having two to twelve carbon atoms respectively such as; for example, ethenyl, propenyl, butenyl, pentenyl, hexenyl, heptenyl, heptdienyl, octenyl, octadienyl, octatrienyl, nonenyl, undecenyl, dodecenyl, and their isomeric forms thereof, preferably an alkenyl group of $R_1$ having four to eight carbon atoms, and an alkenyl group of $R_2$ having two to eight carbon atoms.

The term "$C_{2-12}$ alkynyl" refers to at least one triple bond alkynyl group having two to twelve carbon atoms such as; for example, ethynyl, propynyl, butynyl, pentynyl, hexynyl, heptynyl, octynyl, octadiynyl, octatriynyl, nonynyl, nonediynyl, and their isomeric forms thereof, preferably an alkynyl group of $R_1$ having four to eight carbon atoms, and an alkenyl group of $R_2$ having two to eight carbon atoms.

The term "$C_{3-8}$ cycloalkyl" refers to a cycloalkyl having three to eight carbon atoms such as; for example, cyclopropyl, cyclobutyl, cyclopentyl, cyclohexyl, cycloheptyl, cyclooctyl, and their isomeric forms thereof, preferably an cycloalkyl group having three to six carbon atoms.

The term "$C_{3-8}$ cycloalkenyl" refers to a cycloalkenyl having three to eight carbon atoms such as; for example, cyclopropenyl, cyclobutenyl, cyclopentenyl, cyclohexenyl, cycloheptenyl, cyclooctenyl, and their isomeric forms thereof, preferably an cycloalkyl group having five to six carbon atoms.

The terms "$C_{1-4}$ alkoxy", "$C_{1-6}$ alkoxy", and "$C_{1-8}$ alkoxy" refer to an alkyl group having one to four, one to six, or one to eight carbon atoms respectively attached to an oxygen atom of hydroxyl group such as; for example, methoxy, ethoxy, propyloxy, butyloxy, pentyloxy, hexyloxy, heptyloxy, or octyloxy and their isomeric forms thereof.

The term "aryl" refers to monocarbocyclic or bicarbocyclic aromatic moiety such as; for example phenyl, naphthyl, biphenyl. Each of these moieties may be substituted as appropriate. Aryl is preferably phenyl or phenyl substituted with $C_{1-4}$ alkyl, $C_{1-4}$ alkoxy, fluoro, chloro, bromo, —$NO_2$, —$CF_3$, —$N(C_{1-4}$ alkyl$)_2$, —C(=O)$R_3$, or —NC(=O)$R_3$.

The term "het" refers to a 5- to 10-membered unsaturated heterocyclic moiety having one or more atoms selected from the group consisting of oxygen, nitrogen, and sulfur such as; for example, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzoisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1-indolyl, 1-indazolyl, 2-isoindolyl, 1-purinyl, 3-isothiazolyl, 4-isothiazolyl and 5-isothiazolyl, preferably pyridyl, quionlinyl, pyrrolyl, thienyl, thiazolyl, or indolyl. Each of these moieties may be substituted with one to two $C_{1-4}$ alkyl, —$NO_2$, fluoro, chloro, or bromo as appropriate.

The term "Q" refers to a 5- to 10-membered saturated heterocyclic moiety having one to two atoms selected from the group consisting of oxygen, nitrogen, and sulfur such as; for example, piperidinyl, 2-, 3-, or 4-piperidinyl, [1,4] piperazinyl, morpholinyl, 2- or 3-morpholinyl, thiomorpholinyl, dioxolanyl, imidazolidinyl, [1,3] oxathiolanyl, [1,3]oxazolidinyl, pyrrolidinyl, butyrolactonyl, butyrolactamyl, succinimidyl, glutarimidyl, valerolactamyl, 2,5-dioxo-[1,4]-piperazinyl, pyrazolidinyl, 3-oxopyrazolidinyl, 2-oxo-imidazolidinyl, 2,4-dioxo-imidazolidinyl, 2-oxo-[1,3]-oxazolidinyl, 2,5-dioxo-[1,3]-oxazolidinyl, isoxazolidinyl, 3-oxo-isoxazolidinyl, [1,3]-thiazolidinyl, 2- or 4-oxo-[1,3]-thiazolidinyl, preferably butyrolactamyl, succinimidyl, glutarimidyl, valerolactamyl, 2,5-dioxo-[1,4]-piperazinyl, 3-oxopyrazolidinyl, 2-oxo-imidazolidinyl, 2,4-dioxo-imidazolidinyl, 2-oxo-[1,3]-oxazolidinyl, 2,5-dioxo-[1,3]-oxazolidinyl, 3-oxo-isoxazolidinyl, 2- or 4-oxo-[1,3]-thiazolidinyl.

The term halo refers to fluoro, chloro, bromo, or iodo, preferably fluoro, chloro, or bromo.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

The compounds of formula I of this invention contain a chiral center at the α-position of hydroxamic acids, as such there exist two enantiomers or a racemic mixture of both. This invention relates to both the enantiomers, as well as mixtures containing both the isomers. In addition, depending on the substituents, additional chiral centers and other isomeric forms may be present in any of the $R_2$ groups, and this invention embraces all possible stereoisomers and geometric forms in this group.

$R_1$ is preferably n-butyl, isobutyl, 1-methylpropyl, tert-butyl, n-pentyl, 3-methylbutyl, n-hexyl, n-heptyl, n-octyl, phenyl, 4-methylphenyl, 4-ethylphenyl, 4-tert-butylphenyl, 4-isopropylphenyl, 4-chlorophenyl, 4-bromophenyl, 4-fluorophenyl, 4-trifluoromethylphenyl, 4-methoxyphenyl, 4-ethoxyphenyl, 4-n-butyloxyphenyl, benzyl, 4-phenylbenzyl, 2-, 3-, or 4-fluorobenzyl, 2-, 3-, 4-chlorobenzyl, 2-, 3-, 4-bromobenzyl, and 4-ethoxybenzyl. More preferably $R_1$ is n-butyl, n-pentyl, n-hexyl, n-heptyl, n-octyl, phenyl, 4-methylphenyl, 4-ethylphenyl, 4-isopropylphenyl, 4-chlorophenyl, 4-bromophenyl, 4-fluorophenyl, 4-methoxyphenyl, 4-butoxyphenyl, benzyl, 4-fluorobenzyl, 4-chlorobenzyl, 4-bromobenzyl, and 4-ethoxybenzyl.

$R_2$ is preferably methyl, 1-cyano-1-phenyl methyl, 2-cyano ethyl, 2-phenylethyl, 2-bromo-2-phenylethyl, 2-bromoethyl, propyl, isopropyl, 3-chloropropyl, 3-bromopropyl, n-butyl, isobutyl, 3-methylbutyl, 1-methylpropyl, tert-butyl, n-pentyl, 3-methybutyl, n-hexyl, n-heptyl, n-octyl, n-hexadecyl, n-octadecyl, 2-propenyl, 2-propynyl, 3-butenyl, 4-pentenyl, 3-butenynyl, 4-pentenynyl, cyclopentyl, cyclohexyl, cyclohexylmethyl, 2-cyclohexylethyl, 4-cyclohexylbutyl, dimethylaminoethyl, dimethylaminopropyl, diethylaminopropyl, phenylaminomethyl, phenyl, 4-methylphenyl, 4-chlorophenyl, 4-bromophenyl, 4-fluorophenyl, 4-trifluoromethylphenyl, 2-methoxyphenyl, 4-methoxyphenyl, 4-nitrophenyl, 4-ethoxyphenyl, benzyl, 4-methylbenzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, and 2-methylbenzyl, 3-methylbenzyl, 4-methylbenzyl, 4-ethoxybenzyl, 4-nitrobenzyl, methylcarbonyl, 1-methylcarbonyl methyl, 2-phenylcarbonyl ethyl, isopropylcarbonyl, methoxycarbonyl, ethoxycarbonyl, 1,1-ethoxycarbonyl methyl, 2,2-ethoxycarbonyl ethyl, 1,2-ethoxycarbonyl ethyl, 2-methoxycarbonyl propyl, 3-methoxycarbonyl propyl, 1-ethoxycarbonyl methyl, 1-ethoxycarbonyl ethyl, phenylcarbonyl, phenylcarbonyl methyl, pyridylcarbonyl methyl, pyridylmethyl, pyridylethyl, quionlinylmethyl, pyrrolyl methyl, indolyl methyl, thienyl, thiazolyl, thienylmethyl, thienylethyl, piperdinyl methyl, piperazinyl methyl, morpholino methyl, morpholino ethyl, morpholino propyl, thiomorpholino methyl, thiomorpholino propyl, 4-methoxybenzenesulfonyl methyl, 3-(4-methoxybenzenesulfonyl)amino propyl, 3-(4-methoxybenzenesulfonyl)propyl, 3-hydroxy, amino, 3-phenoxy propyl, 2-phenyl ethyloxy, (4-butoxybenzenesulfonyl) methyl, methyl-3-( 1,5,5-trimethylhydantoin), methyl-3-( 1-butyl-5,5-dimethylhydantoin), (4-methoxybenzenesulfonyl)methyl, (4-chlorobenzenesulfonyl)-methyl, (4-bromobenzenesulfonyl)methyl, (n-butylsulfonyl)methyl, (n-octylsulfonyl)-methyl, 3-(4-methoxybenzenesulfonyl) propyl, (4-methylbenzenesulfonyl)methyl, (benzenesulfonyl)methyl, methyl-3-(1-methylhydantoin), methyl-3-(1-butylhydantoin) and methyl-3-(5,5-dimethylhydantoin). More preferably $R_2$ is (4-methoxybenzenesulfonyl)methyl, (4-chlorobenzenesulfonyl)-methyl, (4-bromobenzenesulfonyl)methyl, (n-butylsulfonyl)methyl, (n-octylsulfonyl)methyl, 3-(4-methoxybenzenesulfonyl) propyl, (4-methylbenzenesulfonyl)methyl, (benzenesulfonyl)methyl, methyl-3-(1-methylhydantoin), methyl-3-(1-butylhydantoin) and methyl-3-(5,5-dimethylhydantoin).

Particularly preferred compounds of this invention are as follows:

(1) N-hydroxy 2-[(4-methoxybenzenesulfonyl) methyl]-3-phenyl-propionamide,
(2) N-hydroxy 2-[(benzenesulfonyl)methyl]-3-phenyl-propionamide,
(3) N-hydroxy 2-[(benzenesulfonyl)methyl]-propionamide,
(4) N-hydroxy-2-[(4-methoxybenzenesulfonyl)methyl]-3-(4-methoxybenzenesulfonyl)-propionamide,
(5) N-hydroxy-2-[(4-chlorobenzenesulfonyl)methyl]-3-(4-chlorobenzenesulfonyl)-propionamide,
(6) N-hydroxy-2-[(4-bromobenzenesulfonyl)methyl]-3-(4-bromobenzenesulfonyl)-propionamide,
(7) N-hydroxy-2-[(n-butylsulfonyl)methyl]-3-(n-butylsulfonyl)-propionamide, (8) N-hydroxy-2-[(n-octylsulfonyl)methyl]-3-(n-octylsulfonyl)-propionamide, (9) N-hydroxy-2-[(4-methylbenzenesulfonyl)methyl]-3-(4-methylbenzenesulfonyl)-propionamide,

(10) N-hydroxy-2-[(benzenesulfonyl)methyl]-3-(benzenesulfonyl)-propionamide,

(11) N-hydroxy-2-[(4-methoxybenzenesulfonyl)methyl]-5-(4-methoxybenzenesulfonyl)-pentanamide,

(12) N-hydroxy-2-[(n-octylsulfonyl)methyl]-3-(4-methoxybenzenesulfonyl)-propionamide,

(13) N-hydroxy-2-[methyl-3-(1-methylhydantoin)]-3-(4-methoxybenzenesulfonyl)-propionamide,

(14) N-hydroxy-2-[methyl-3-(1-butylhydantoin)]-3-(4-butoxybenzenesulfonyl)-propionamide,

(15) N-hydroxy-2-[methyl-3-(1-butylhydantoin)]-3-(4-methoxybenzenesulfonyl)-propionamide,

(16) N-hydroxy-2-[methyl-3-(5,5-dimethylhydantoin)]-3-(4-methoxybenzene-sulfonyl)-propionamide,

(17) (+)-N-hydroxy-2-[(n-octylsulfonyl)methyl]-3-(4-methoxybenzenesulfonyl)-propionamide,

(18) (−)-N-hydroxy-2-[(n-octylsulfonyl)methyl]-3-(4-methoxybenzenesulfonyl)-propionamide,

(19) (+)-N-hydroxy-2-[methyl-3-(1-methylhydantoin)]-3-(4-methoxybenzenesulfonyl)-propionamide

(20) (−)-N-hydroxy-2-[methyl-3-(1-methylhydantoin)]-3-(4-methoxybenzenesulfonyl)-propionamide

(21) (+)-N-hydroxy-2-[methyl-3-(1-butylhydantoin)]-3-(4-butoxybenzenesulfonyl)-propionamide,

(22) (−)-N-hydroxy-2-[methyl-3-(1-butylhydantoin)]-3-(4-butoxybenzenesulfonyl)-propionamide,

(23) (+)-N-hydroxy-2-[methyl-3-(1-butylhydantoin)]-3-(4-methoxybenzenesulfonyl)-propionamide,

(24) (−)-N-hydroxy-2-[methyl-3-(1-butylhydantoin)]-3-(4-methoxybenzenesulfonyl)-propionamide,

(25) (+)-N-hydroxy-2-[methyl-3-(5,5-dimethylhydantoin)]-3-(4-methoxybenzenesulfonyl)-propionamide, or

(26) (−)-N-hydroxy-2-[methyl-3-(5,5-dimethylhydantoin)]-3-(4-methoxybenzenesulfonyl)-propionamide.

The compounds of this invention can be prepared in accordance to the process discussed below.

In Scheme I, $R_1$ and $R_2$ are the groups as defined previously. Substituted malonate esters 2 are either obtained commercially, or can be readily prepared from structure 1 by methods well known to those skilled in the art. For example, reaction of an enolate of structure 1, generated by an appropriate base in an appropriate solvent, with an alkylating agent $R_2$-I (I is bromo, chloro, tosylate, mesylate, epoxides, etc.) provides the desired substituted malonate esters 2. See: *Organic Synthesis*, Vol. 1 p 250 (1954); *Organic Synthesis*, Vol. 3, p 495 (1955). Compound 2 is hydrolyzed to mono-acid compound 3 by reaction with one equivalent of an appropriate base such as alkali hydroxide in an appropriate solvent at a temperature ranging from 0° C. to 30° C. In the presence of formaldehyde and piperidine in an appropriate solvent such as pyridine, ethanol, dioxane at refluxing temperatures, compound 3 is converted to acrylic esters 4. In many cases, acrylic esters 4 are commercially available. A thiol (H-$SR_1$) is add to the acrylic ester 4 at room temperature to afford sulfide esters 5 in the presence of either a catalytic amount of alkoxide in alcoholic solvent or a tertiary amine base in chloroform. The resultant sulfides 5 are readily oxidized to sulfones 6 by an oxidizing agent such as meta-chloroperbenzoic acid (MCPBA) in an appropriate solvent such as methylene chloride, or using hydrogen peroxide in acetic acid as a solvent. The esters can be hydrolyzed by procedures well known in the art such as using 6N HCl and refluxing for 10 to 20 hours or using iodotrimethylsilane in chloroform to afford free acids 7. Coupling of acids 7 with hydroxylamine hydrochlorides to form hydroxamates 9 may be achieved by several routes well known to those skilled in the art. For example, acids 7 can be activated by chloroethylformate in dry THF or a similar compatible solvent, or by a carbodiimide condensing agent such as EDC, with or without HOBT, in DMF and methylene chloride. A tertiary amine is required in both situations. The subsequent reaction of activated 7 with hydroxylamine provides the desired hydroxamic acid derivatives. Alternatively, acids 7 may be condensed, using the same reagents as described above, with benzyl-protected hydroxylamine hydrochloride, to produce the protected hydroxamates 8. Compounds 8 are often easier to purify, and may readily be hydrogenolytically cleaved to the free hydroxamates 9 by a palladium catalyst in alcoholic solvents. Other protected hydrocylamines such as tert-butyl hydroxylamine may also be used, and the free hydroxamate can be obtained by treating it with trifluoroacetic acid.

A second method of preparing the compounds of the invention is to utilize commercially available acrylic acids 10 as shown in Scheme II. Treatment of acrylic acids with thiols affords compounds 11. The reaction may be accomplished in refluxing an appropriate solvent such as dioxane with piperidine as a catalyst. See: *Annelen*, Vol. 564, pp 73–78 (1949). A variation of this method is shown in Scheme III in which ax-bromomethyl acrylic acids 12 are reacted with two moles of thiols to afford bis-sulfides 13. Oxidation of the resulting sulfides with meta-chloroperbenzoic acid or with excess hydrogen peroxide provides compound 7 in Scheme II and compound 14 in Scheme III, respectively. The remaining synthetic steps which lead to products 9 and 15 are similar to the procedures outlined in Scheme I.

Schemes IV, V and VI depict methods especially adapted to the preparation of the compounds of formula I wherein the $R_2$ group contains heteroatoms. In Scheme IV, substituent $R_4$ is defined as previously. Group I in structure 16 is bromo, chloro, tosylate, mesylate, or epoxides, and may be replaced by an agent $R_4$-X-H according to procedures well known in the art (X may be O, $NR_7$, S and etc.). The remaining synthetic steps which lead to compound 18 are similar to the procedures outline in Scheme I.

In Scheme V a suitably protected cysteine (P in structure 19 is a protecting group) can be converted to the corresponding thiol 20. After removing the protecting group, a $R_7$ group (as defined previously) can be introduced into the nitrogen atom as shown in structure 23. The procedure outlined in Scheme V is discussed in further detail in Synthesis Communication, Vol. 16, No. 5, p. 565 (1986). This method can be carried out for both the racemate or a single enantiomer. Following the general procedures as described above but starting with enantiomerically enriched isomers, the desired single enantiomer, either R or S can be obtained.

In Scheme VI, structure 12 is first reacted with one equivalent of thiol or sulfinate in a suitable solvent such as toluene in the absence or presence of a suitable base such as sodium bicarbonate or triethyl amine, at ambient temperature or reflux, to afford 25 or 26, respectively. Conversion of 25 to 26 is accomplished with an oxidant such as meta-chloroperbenzoic acid, in a suitable solvent such as methylene chloride at 0° C. Intermediate 26 is reacted with the anion or conjugate acid of W (wherein W is a group attached via a heteroatom such as oxygen, nitrogen or sulfur) in a solvent such as toluene or dimethylformamide, in the absence or presence of a basic catalyst such as sodium bicarbonate or triethyl amine, preferably at reflux to provide intermediate 7, in which the $R_2$ group may be —$CH_2XR_4$, —$CH_2$-het, or —$CH_2$-Q. The remaining synthetic steps which lead to final hydroxamic products 9 are similar to the procedures outlined in Scheme I.

In addition to Schemes IV, V and VI, the compounds of formula I wherein the $R_2$ group contains heteroatoms may also be prepared according to Scheme II by using structure 12. In this method, α-bromomethyl acrylic acid 12 is reacted with one equivalent of anion or conjugate acid of W to provide acrylic acids 10, in which the $R_2$ group may be —$CH_2$-W (wherein W is as defined above). The remaining synthetic steps which lead to final hydroxamic products 9 are similar to the procedures outlined in Scheme II. When W is a thiol or thiolate, the sulfur contained in $R_2$ may be oxidized to a sulfoxide or sulfone, give rise to, for example, unsymmetrical bis-sulfonyl hydroxamates.

The chemistry in Schemes I, II, IV and VI proceeds through achiral or racemic intermediates and pure enantiomers of the final products may be obtained by resolution of intermediates 5–9 or 11 by chiral chromatography or classical derivatization methods such as chiral salt formation of intermediate 7.

The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating a patient, suffering from or susceptible to diseases involving connective tissue degradation, or inhibiting various enzymes from the matrix metalloproteinase family, including collagenase, stromelysin, and gelatinase, the compounds or pharmaceutical compositions thereof will be administered orally, parenterally and/or topically at a dosage to obtain and maintain a concentration, that is, an amount, or blood-level of active component in the patient undergoing treatment which will be effective to inhibit such enzymes. Generally, an effective amount of the active compound will be in the range of about 0.1 to about 100 mg/kg. It is to be understood that the dosages may vary depending upon the requirements of the patient, the severity of connective tissue degradation being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of the present invention inhibit various enzymes from the matrix metalloproteinase family, predominantly stromelysin and gelatinase, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation. Such diseases and conditions are well known and readily diagnosed by physician of ordinary skill.

Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as; for example, water-for-injection and a suitably buffered isotonic solution having a pH of about 3.5–6. Suitable buffering agents include; for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned inhibitory effective amount of dosage. The compounds of formula I according to this invention are advantageously administered orally in solid and liquid dosage forms.

The compounds and their preparations of the present invention will be better understood in connection with the following examples, which are intended as an illustration of and not a limitation upon the scope of the invention.

EXAMPLE 1

Preparation of N-hydroxy 2-[(4-methoxybenzenesulfonyl) methyl]-3-phenyl-propionamide.

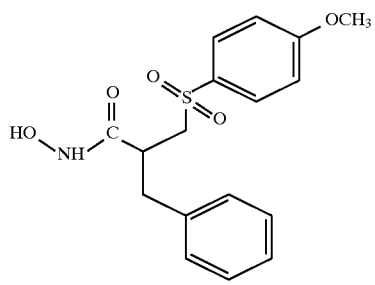

Step 1 Preparation of benzylmalonic acid monoethyl ester.

Benzylmalonic acid diethyl ester (10 g, 40 mmol) in 25 mL of ethanol is cooled to 0° C. Potassium hydroxide (2.5 g, 40 mmol) dissolved in 25 mL of ethanol is added dropwise over 50 minutes. The cooling bath is removed and the mixture is stirred for one additional hour. The volume of solvent is reduced by evaporation in vacuo, and the residual solution is poured into aqueous sodium bicarbonate solution and extracted twice with ethyl acetate. The aqueous phase is acidified with aqueous 10% HCl and extracted twice with ethyl acetate. The organic phase is dried with a brine extraction, filtered from anhydrous sodium sulfate, and concentrated in vacuo, yielding 8.08 g of the title compound as a colorless oil.

Step 2 Preparation of 2-benzyl-2-propenoic acid ethyl ester.

Benzylmalonic acid monoethyl ester (8.0 g, 36 mmol), 7 mL of pyridine, 0.36 mL (3.6 mmol) of piperidine, and 1.06 g (35 mmol) of paraformaldehyde is refluxed under nitrogen for 1.5 hours in an oil bath maintained at 130° C. After cooling for 0.5 hours the mixture is partitioned between 100 mL of water and 100 mL of hexane. The aqueous phase is re-extracted with 50 mL of hexane. The organic phase is washed with aqueous 10% HCl, water, 1M sodium bicarbonate, and brine. It is dried over anhydrous sodium sulfate and concentrated in vacuo, yielding 5.8 g of the title compound as a colorless oil.

Step 3 Preparation of 2-[(4-methoxybenzenethio)methyl]-3-phenyl-propenoic acid ethyl ester.

4-Methoxybenzenethiol (0.6 mL, 4.7 mmol) in 1 mL of ethanol is cooled in an ice bath with stirring. Ethanolic sodium ethoxide solution 0.13 ml (0.34 mmol) is added. After 15 minutes 1.0 g (5.3 mmol) of 2-benzyl-2-propenoic acid ethyl ester in 1 mL of ethanol is added dropwise over about 2 minutes. The ice bath is removed and the reaction mixture is allowed to stir for 17 hours. The mixture is evaporated in vacuo and partitioned between ethyl acetate and aqueous 5% HCl. The organic phase is concentrated and chromatographed over silica gel, eluting with hexane:acetone (98:2), to afford 1.04 g of the title compound as a colorless oil.

Step 4 Preparation of 2-[(4-methoxybenzenesulfonyl)methyl]-3-phenyl-propionic acid ethyl ester.

To a solution of 2-[(4-methoxybenzenethio)methyl]-3-phenyl-propionic acid ethyl ester (1.51 g, 4.6 mmol) in 50 mL of methylene chloride, cooled in an ice bath, is added 2.17 g (10 mmol) of solid MCPBA portion wise over 5 minutes. The cooling bath is removed, and the mixture is stirred at room temperature overnight. The suspension is filtered and the solids washed with methylene chloride. The organic solution is extracted with three portions of 1M sodium bicarbonate, dried by extraction with brine, filtered from anhydrous sodium sulfate, and concentrated. Chromatography on silica gel, eluting with methylene chloride:acetone (99:1), afforded 1.31 g of the title compound as a colorless oil.

Step 5 Preparation of 2-[(4-methoxybenzenesulfonyl)methyl]-3-phenyl-propionic acid.

A mixture of 0.56 g (1.5 mmol) of 2-[(4-methoxybenzenesulfonyl)methyl]-3-phenyl-propanoic acid ethyl ester and 8 ml of 6N HCl is heated at 115° C. for 17 hours. The mixture is transferred to 100 ml of ice-water and extracted with two portions of ethyl acetate. The organic phase is extracted with three 50 mL portions of aqueous 5% sodium bicarbonate. The bicarbonate solution is poured over ice and acidified with concentrated HCl. The acidified aqueous mixture is extracted with three 50 mL portions of ethyl acetate and the combined organic extracts are concentrated in vacuo to yield 0.45 g of the title compound as a white solid.

Step 6 Preparation of N-benzyloxy-2-[(4-methoxybenzenesulfonyl)methyl]-3-phenyl-propionamide.

A solution of 2-[(4-methoxybenzenesulfonyl)methyl]-3-phenyl-propionic acid (1.05 g, 3.14 mmol) and 0.69 mL (6.3 mmol) of NMM in dry THF, under nitrogen, is cooled in an ice bath. Ethyl chloroformate (0.33 mL, 3.5 mmol) in 7 mL of THF is added dropwise over 5 minutes. The suspension is stirred at 0° C. for 10 minutes, after which a slurry of O-benzylhydroxylamine hydrochloride (0.64 g, 4 mmol) and NMM (0.44 mL, 4 mmol) in 7 mL of THF is introduced in several portions. The mixture is stirred for 10 minutes and stored at 10° C. overnight. The mixture is allowed to warm to room temperature for 0.5 hours, and is then partitioned between ethyl acetate and aqueous 10% HCl. The organic phase is washed with water, three portions of 1M sodium bicarbonate and brine. It is dried over anhydrous sodium sulfate, concentrated and chromatographed on silica gel, eluting with 40%–50% ethyl acetate in hexanes. This affords 1.26 g of the title compound as a colorless oil.

Step 7 Preparation of N-hydroxy-2-[(4-methoxybenzenesulfonyl)methyl]-3-phenyl-propionamide.

N-benzyloxy-2-[(4-methoxybenzenesulfonyl)methyl]-3-phenyl- propionamide (1.25 g, 2.85 mmol) is dissolved in 45 mL of ethanol. To this is added 0.36 g of palladium hydroxide on carbon (Pearlman's catalyst), and the suspension is placed in a shaker under 15 psi of hydrogen for 2.25 hours. The catalyst is filtered off, washing with ethanol, and the ethanol solution is concentrated in vacuo to afford, after evaporation from methylene chloride, 0.875 g of the title compound as a white solid.

$^1$H NMR (DMSO) δ 10.6, 8.8, 7.67, 7.17–7.22, 7.03–7.1, 3.85, 3.55, 3.02, 2.76–2.79, 2.62; $^{13}$C NMR (DMSO) δ 168.7, 164.1, 138.5, 131.3, 130.7, 129.7, 129.1, 127.3, 115.4, 56.5, 56.5, 38.3, 37.3; MS (EI) m/z 349, 317, 288, 214, 171, 155, 145, 117, 107, 91.

EXAMPLE 2

Preparation of N-hydroxy 2-[(benzenesulfonyl)methyl]-3-phenyl-propionamide.

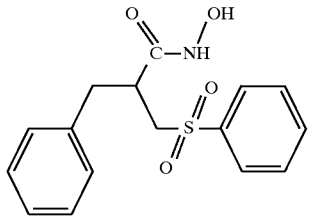

Following the general procedure outlined in EXAMPLE 1 (steps 3 to 7) and making non-critical variations but starting with thiophenol in step 3, the title compound is obtained as a white solid.

$^1$H NMR (DMSO) δ 10.6, 8.8, 7.73, 7.58, 7.17, 7.02, 3.60, 3.07, 2.81–2.7, 2.65–2.60; $^{13}$C NMR (DMSO) δ 168.2, 139.4, 138.1, 134.3, 129.9, 129.3, 128.8, 128.0, 126.9, 60.2, 55.8, 38.4; IR (mull) cm$^{-1}$ 3346, 2925, 1633, 1525, 1450, 1284, 1139; MS (EI) m/z 319, 287, 184, 164, 145, 125, 117, 91. Calculated for $C_{16}H_{17}NO_4S$: C, 60.17; H, 5.36; N, 4.39; S, 10.04; Found: C, 60.04; H, 5.46; N, 4.28; S, 9.88.

EXAMPLE 3
Preparation of N-hydroxy 2-[(benzenesulfonyl)methyl]-propionamide.

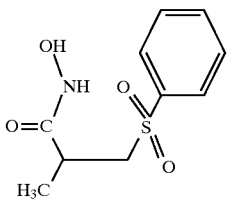

Step 1 Preparation of 2-[(benzenesulfonyl)methyl]-propionoic acid

To 1 mmol of 2-[(benzenethio)methyl]-propionic acid in 10 mL of methylene chloride cooled in an ice bath is added 0.5 g (2.3 mmol) of solid MCPBA in several portions. The reaction mixture is stirred at room temperature for 6 hours, and refrigerated overnight. The suspension is filtered, and the filtrate is concentrated and chromatographed on silica gel, eluting with 25% ethyl acetate and 0.5% acetic acid in hexanes, followed by 50% ethyl acetate, 0.5% acetic acid, in hexanes. Evaporation of the solvents left 0.225 g of the title compound as a white solid.

Step 2 Preparation of N-hydroxy 2-[(benzenesulfonyl) methyl]-propionamide.

Following the general procedure outlined in EXAMPLE 1 (steps 6–7) and making non-critical variations but starting with 2-[(benzenesulfonyl)methyl]-propionoic acid in step 6, the title compound is obtained as a white solid.

$^1$H NMR (DMSO) δ 10.6, 8.8, 7.87, 7.74, 7.64, 3.53, 3.27, 2.58, 1.05; $^{13}$C NMR (DMSO) δ 170.0, 139.8, 134.4, 129.9, 128.0, 57.6, 32.3, 19.0; MS (EI) m/z 243, 211, 141, 125, 77.

EXAMPLE 4
Preparation of N-hydroxy-2-[(4-methoxybenzene-sulfonyl) methyl]-3-(4-methoxybenzenesulfonyl)-propionamide

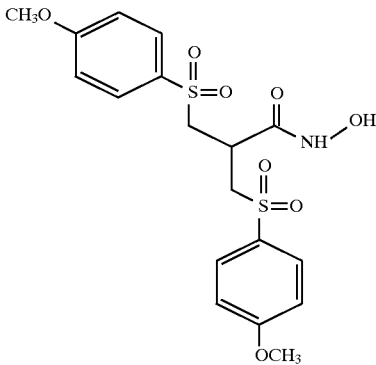

Step 1 Preparation of 2-(4-methoxybenzenethiomethyl)-3-(4-methoxybenzenethio)-propionic acid.

To a stirred mixture of 2-bromomethylacrylic acid (10 g, 60 mmol) in 125 mL of toluene at room temperature, is added sodium bicarbonate (15 g, 180 mmol) and 4-methoxybenzenethiol (16.5 mL, 140 mmol) and this mixture is refluxed overnight. The mixture is partitioned between aqueous sodium bicarbonate and ethyl acetate, the aqueous phase is acidified to pH 2 with concentrated hydrochloric acid, and extracted with ethyl acetate. The combined organic extracts are concentrated in vacuo to afford the title compound as white solid.

$^1$H NMR (DMSO) δ 12.1, 7.25, 6.85, 3.74, 3.05, 2.50; $^{13}$C NMR (DMSO) δ 174.60, 159.59, 134.05, 125.57, 115.66, 55.93, 55.63, 45.38, 36.93.

Step 2 Preparation of 2-(4-methoxybenzenesulfonylmethyl)-3-(4-methoxybenzenesulfonyl)-propionic acid.

A stirred mixture of 2-(4-methoxybenzenethiomethyl)-3-(4-methoxybenzenethio)-propionic acid (18.5 g, 5 mmol) in methylene chloride (250 mL) is cooled in a dry ice/acetone bath and m-chloroperoxybenzoic acid (MCPBA) (54.5 g, 213 mmol) is added in small portions over approximately 30 minutes. After stirring at ambient temperature for two days and standing for one day the mixture is filtered in vacuo over a plug of silica gel 60 (230–400 mesh) and the filtrand is eluted with chloroform followed by chloroform/methyl alcohol/acetic acid (89:10:1). The filtrate is concentrated and triturated with hexane to afford the title compound as a white solid.

m.p. 174°–5° C.; MS (FAB) m/z 430, 429, 239, 171, 109, 107, 103, 89, 61; $^1$H NMR (DMSO) δ 7.66, 7.12, 3.86, 3.57, 2.69; $^{13}$C NMR (DMSO) δ 171.57, 163.97, 130.61, 130.12, 115.13, 56.28, 55.84, 30.04.

Step 3 Preparation of N-benzyloxy-2-(4-methoxybenzenesulfonylmethyl)-3-(4-methoxybenzenesulfonyl)-propionamide.

A mixture of 2-(4-methoxybenzenesulfonylmethyl)-3-(4-methoxybenzenesulfonyl)-propionic acid (5.0 g, 12 mmol) in tetrahydrofuran (30 mL), 1-(3-dimethylaminopropyl)-3-ethylcarbodiimide hydrochloride (4.3 g, 23 mmol), benzyl-hydroxylamine hydrochloride (2.3 g, 14 mmol), and distilled water (30 mL) is stirred overnight. The mixture is filtered to yield a white precipitate which is dissolved in chloroform (200 ml) and filtered. The filtrate is extracted with brine (100 mL) and the organic phase concentrated in vacuo, to yield N-benzyloxy-2-(4-methoxybenzenesulfonylmethyl)-3-(4-methoxybenzenesulfonyl)-propionamide (2.24 g, 36%). The initial filtrate from the overnight reaction is transferred to ethyl acetate and extracted with 10% hydrochloric acid, water, aqueous sodium bicarbonate, and brine, and concentrated in vacuo to also yield the title compound as a white solid.

m.p. 151° C. (dec.);. $^1$H NMR (DMSO) δ 11.5, 7.70, 7.37, 7.13, 4.69, 3.86, 3.50, 2.80; $^{13}$C NMR (DMSO) δ 166.68, 164.31, 136.72, 130.96, 130.93, 129.65, 129.09, 115.51, 77.56, 56.65, 56.34, 55.72, 34.00.

Step 4 Preparation of N-hydroxy-2-(4-methoxybenzenesulfonylmethyl)-3-(4-methoxybenzenesulfonyl)-propionamide.

A suspension of N-benzyloxy-2-(4-methoxybenzenesulfonylmethyl)-3-(4-methoxybenzenesulfonyl)-propionamide (5.0 g, 9.4 mmol), Pearlman's catalyst (0.9 g), and ethyl alcohol (50 mL) is agitated under hydrogen (20 psig) at room temperature overnight. The reaction mixture is filtered through celite and the soluble solids dissolved with methyl alcohol followed by chloroform/methyl alcohol (9:1). The combined filtrates are concentrated in vacuo to yield N-hydroxy-2-(4-methoxybenzenesulfonylmethyl)-3-(4-methoxybenzenesulfonyl)-propionamide as a white solid.

m.p. 173.5°–4.5° C.; IR (mull) 3292, 1640, 1597, 1579, 1500, 1320, 1313, 1304, 1294, 1282, 1266, 1145, 1089, 1023, 838 cm$^{-1}$; $^1$H NMR (DMSO) δ 10.9, 8.9, 7.69, 7.12, 3.87. 3.48, 2.82; $^{13}$C NMR (DMSO) δ 166.13, 163.93, 130.55, 130.20, 115.15, 55.24, 55.97, 33.47.

EXAMPLE 5

Preparation of N-hydroxy-2-[(4-chlorobenzenesulfonyl)methyl]-3-(4-chlorobenzenesulfonyl)-propionamide.

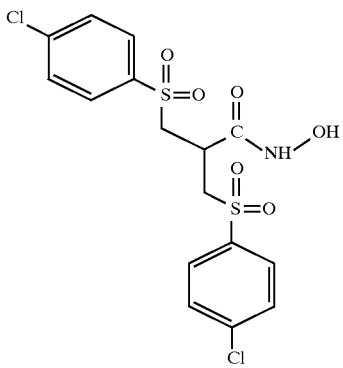

Step 1 Preparation of 2-(4-chlorobenzenesulfonylmethyl)-3-(4-chlorobenzenesulfonyl)-propionic acid.

Following the general procedure in EXAMPLE 4 (steps 1 and 2) and making non-critical variations but starting with 4-chlorothiophenol in step 1, the title compound is obtained as a white solid.

m.p. 197° C. (dec.); $^1$H NMR (DMSO) δ 7.77, 7.67, 3.74, 3.54, 2.58; $^{13}$C NMR (DMSO) δ 171.24, 139.38, 138.34, 130.26, 129.91, 56.66, 37.59.

Step 2 Preparation of N-hydroxy-2-[(4-chlorobenzenesulfonyl)methyl]-3-(4-chlorobenzenesulfonyl)-propionamide.

A mixture of 2-(4-chlorobenzenesulfonylmethyl)-3-(4-chlorobenzenesulfonyl)-propionic acid (0.52 g, 1.1 mmol), 1-hydroxybenzotriazole hydrate (0.16 g, 1.2 mmol), 1-(3-dimethylaminopropyl)-3-ethylcarbodiimide hydrochloride (0.25 g, 1.3 mmol), and hydroxylamine hydrochloride (0.083 g, 1.2 mmol) is stirred in an ice bath for 20 minutes and 4-methylmorpholine (0.28 mL, 2.5 mmol) in dimethylformamide (10 mL) is added. After stirring overnight at ambient temperature, the mixture is partitioned between ethyl acetate and aqueous 10% hydrochloric acid. The organic phase is further extracted with aqueous acid, aqueous sodium bicarbonate, brine, dried over anhydrous sodium sulfate, concentrated in vacuo. The concentrate is chromatographed over silica gel (230–400 mesh) with chloroform/acetone/acetic acid (79/20/1) and the eluate concentrated in vacuo, to yield the title compound as a white solid.

m.p. 196°–7.5° C.; MS (FAB) m/z 452, 439, 437, 278, 243, 161, 159, 111; $^1$H NMR (DMSO) δ 10.8, 8.93, 7.78, 7.70, 3.59, 2.77; $^{13}$C NMR (DMSO) δ 165.72, 140.09, 138.08, 130.66, 130.48, 56.01, 33.67.

EXAMPLE 6

Preparation of N-hydroxy-2-[(4-bromobenzenesulfonyl)methyl]-3-(4-bromobenzenesulfonyl)-propionamide.

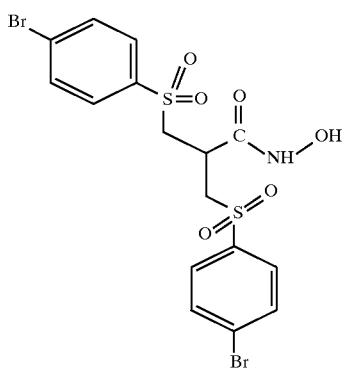

Following the general procedure outlined in EXAMPLE 5 (steps 1 and 2) and making non-critical variations but starting with 4-bromothiophenol in step 1, the title compound is obtained as a white solid.

m.p. 187° C. dec.; MS (FAB) m/z 469, 421, 291, 245, 71, 69, 57, 55, 43, 41; $^1$H NMR (DMSO) δ 10.9, 8.96, 7.85, 7.70, 3.61, 2.79; $^{13}$C NMR (DMSO) δ 165.75, 138.55, 133.42, 130.67, 129.25, 56.01, 33.65.

EXAMPLE 7

Preparation of N-hydroxy-2-[(n-butylsulfonyl)methyl]-3-(n-butylsulfonyl)-propionamide.

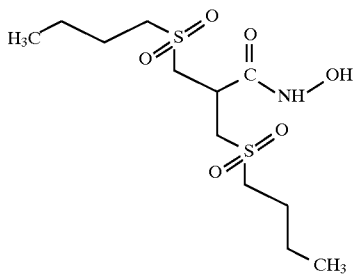

Step 1 Preparation of 2-[(n-butylthio)methyl]-3-(n-butylthio)-propionic acid, ethyl ester.

A mixture of 4-bromomethylacrylic acid, ethyl ester (1.0 g, 6.0 mmol), n-butylthiol (1.4 mL, 13 mmol), potassium carbonate (1.7 g, 13 mmol) in absolute ethyl alcohol (25 mL) is stirred at ambient temperature overnight. The mixture is transferred to ethyl acetate, extracted with aqueous 10% hydrochloric acid, and concentrated in vacuo, to afford the title compound as a clear, colorless oil.

$^1$H NMR (DMSO) δ 4.07, 2.72, 2.47, 1.47, 1.36, 1.18, 0.86; $^{13}$C NMR (DMSO) δ 173.08, 60.65, 46.36, 32.89, 31.61, 21.72, 14.52, 13.90.

Step 2 Preparation of 2-[(n-butylsulfonyl)methyl]-3-(n-butylsulfonyl)-propionic acid, ethyl ester.

After cooling a stirred mixture of 2-[(n-butylthio)methyl]-3-(n-butylthio)-propanoic acid, ethyl ester (1.0 g, 3.4 mmol) in methylene chloride (30 mL), m-chloroperoxybenzoic acid (3.0 g; 14. mmol) is added and the mixture is stirred overnight at ambient temperature. The mixture is filtered and the filtrate concentrated in vacuo to afford 2-[(n-butylsulfonyl)methyl]-3-(n-butylsulfonyl)-propanoic acid, ethyl ester as a clear, colorless oil.

$^1$H NMR (DMSO) δ 4.10, 3.51, 3.38, 3.14, 1.63, 1.39, 1.18, 0.85; $^{13}$C NMR (DMSO) δ 170.99, 61.79, 52.82, 52.53, 34.20, 23.72, 21.40, 14.22, 13.89.

Step 3 Preparation of 2-[(n-butylsulfonyl)methyl]-3-(n-butylsulfonyl)-propionic acid.

A mixture of 2-[(n-butylsulfonyl)methyl]-3-(n-butylsulfonyl)-propanoic acid, ethyl ester (1.0 g, 3.0 mmol) in 6N hydrochloric acid ( 20 mL) is refluxed overnight. The mixture is transferred to distilled water and extracted with ethyl acetate. The combined organic extracts are concentrated in vacuo to yield the title compound as a clear, colorless oil.

$^1$H NMR (DMSO) δ 3.50, 3.30, 3.14, 1.62, 1.37, 0.87; $^{13}$C NMR (DMSO) δ 172.33, 52.88, 52.48, 34.49, 23.75, 21.41, 13.88.

Step 4 Preparation of N-hydroxy-2-[(n-butylsulfonyl) methyl]-3-(n-butylsulfonyl)-propionamide.

Following the general procedure outlined in EXAMPLE 4 (steps 3 and 4) and making non-critical variations but starting with 2-[(n-butylsulfonyl)methyl]-3-(n-butylsulfonyl)-propionoic acid in step 3, the title compound is obtained as a white solid.

$^1$H NMR (DMSO) δ 10.9, 9.0, 3.37, 3.15, 3.09, 1.63, 1.38, 0.88; $^{13}$C NMR (DMSO) δ 166.52, 52.93, 52.55, 32.58, 23.73, 21.43, 13.90.

EXAMPLE 8

Preparation of N-hydroxy-2-[(n-octylsulfonyl)methyl]-3-(n-octylsulfonyl)-propionamide.

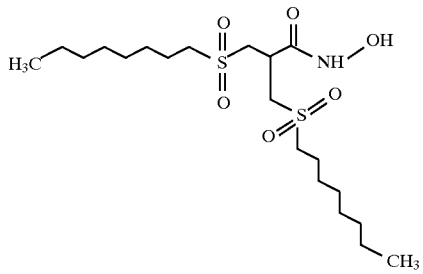

Following the general procedure outlined in EXAMPLE 7 (steps 1 to 4) and making non-critical variations but starting with n-octylthiol in step 1, the title compound is obtained as a white solid.

$^1$H NMR (DMSO) δ 10.9, 9.05, 3.40, 3.08, 1.61, 1.32, 1.23, 0.84; MS (FAB) m/z 456, 440, 245, 133, 71, 69, 57, 55, 43, 41; $^{13}$C NMR (DMSO) δ 166.53, 52.92, 52.77, 32.60, 31.64, 28.90, 28.87, 28.14, 22.51, 21.71, 14.40.

EXAMPLE 9

Preparation of N-hydroxy-2-[(4-methylbenzenesulfonyl)methyl]- 3-(4-methylbenzenesulfonyl)-propionamide.

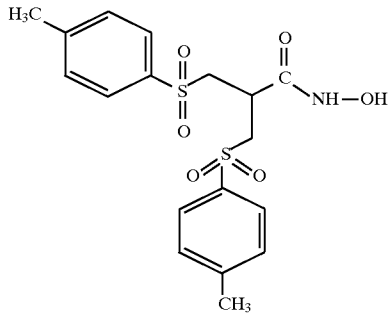

Step 1 Preparation of 2-[(4-methylbenzenesulfonyl)methyl] -3-(4-methylbenzenesulfonyl)propionic acid.

A mixture of 2-bromomethylacrylic acid (2.0 g, 12 mmol), p-toluenesulfinic acid, sodium salt, monohydrate (6.4 g, 27 mmol), and sodium bicarbonate (1.0 g, 12 mmol) in toluene (50 mL) is refluxed overnight. The mixture is transferred to ethyl acetate and extracted with aqueous 10% hydrochloric acid. The organic phase is concentrated in vacuo, and triturated with hexane to yield the title compound as a white solid.

$^1$H NMR (DMSO) δ 7.66, 7.41, 3.47, 2.82, 2.69; $^{13}$C NMR (DMSO) δ 171.46, 145.33, 135.72, 130.44, 128.29, 55.47, 36.15, 21.60.

Step 2 Preparation of N-hydroxy-2-[(4-methylbenzenesulfonyl)methyl]-3-(4-methylbenzenesulfonyl)-propionamide.

To N-methylpyrrolidinone (20 mL) cooled in an ice bath, is added 2-[(4-methylbenzenesulfonyl)methyl]-3-(4-methylbenzenesulfonyl)-propionoic acid (4.4 g, 11 mmol), 1-(3-dimethylaminopropyl)-3-ethylcarbodiimide hydrochloride (4.2 g, 22 mmol), and hydroxylamine hydrochloride (1.5 g, 22 mmol). After stirring overnight at ambient temperature, the mixture is transferred to ethyl acetate and extracted with aqueous 10% hydrochloric acid, distilled water, aqueous sodium bicarbonate, brine, and dried over anhydrous sodium sulfate. The organic phase is concentrated in vacuo and triturated from hexane to afford the title compound as a white solid.

$^1$H NMR (DMSO) δ 10.9, 8.9, 7.62, 7.41, 3.47, 2.82, 2.42; $^{13}$C NMR (DMSO) δ 165.94, 145.12, 136.19, 130.42, 128.37, 55.87, 33.34, 21.61.

EXAMPLE 10

Preparation of N-hydroxy-2-[(benzenesulfonyl)methyl]-3-(benzenesulfonyl)-propionamide.

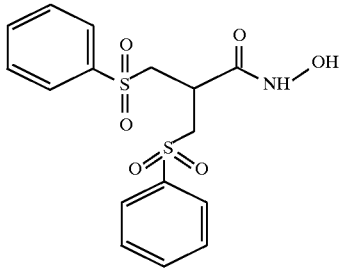

Following the general procedure outlined in EXAMPLE 9 and making non-critical variations but starting with benzenesulfinic acid, sodium salt (2.5 g, 15 mmol) in step 1, the title compound is afforded as a white solid.

Found: C, 50.06; H, 4.56; N, 3.7; S, 16.44; MS (FAB) m/z 386, 385, 384, 383, 351, 279, 242, 209, 149, 125; $^1$H NMR (DMSO) δ 10.9, 8.9, 7.75, 7.66, 3.53, 2.86; $^{13}$C NMR (DMSO) δ 165.83, 139.03, 134.62, 130.02, 128.21, 55.77, 33.19.

EXAMPLE 11
Preparation of N-hydroxy-2-[(4-methoxybenzenesulfonyl)-methyl]-5-(4-methoxybenzenesulfonyl)-pentanamide.

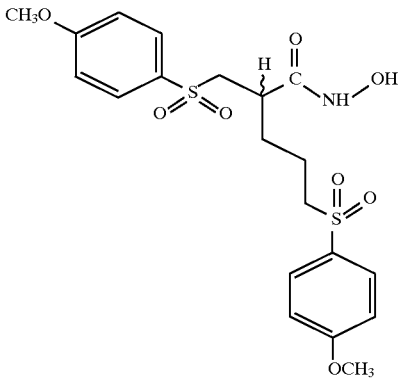

Step 1 Preparation of 3-(4-methoxybenzenethio)-propylmalonic acid, diethyl ester.

To a stirred mixture of 3-chloropropylmalonic acid, diethyl ester (2.1 g, 8.6 mmol) in dimethylformamide (20 mL) is added 4-methoxybenzenethiol (1.2 mL, 9.5 mmol) in dimethylformamide (20 mL) and sodium bicarbonate (0.72 g, 8.6 mmol). After stirring overnight at room temperature the mixture is transferred to ethyl acetate and extracted with aqueous 10% hydrochloric acid, distilled water, aqueous sodium bicarbonate, brine, and concentrated in vacuo. The concentrate is triturated with hexane, extracted with distilled water, concentrated in vacuo, and chromatographed over silica gel with methylene chloride/hexane (9/1) to yield the title compound as a clear, colorless oil.

$^1$H NMR (DMSO) δ 7.29, 6.89, 4.08, 3.73, 3.45, 2.83, 1.85, 1.49, 1.14; $^{13}$C NMR (DMSO) δ 169.66, 159.19, 133.05, 126.51, 115.52, 61.66, 55.99, 51.48, 34.65, 28.00, 27.01, 14.70.

Step 2 Preparation of 3-(4-methoxybenzenesulfonyl)-propylmalonic acid, diethyl ester.

A stirred mixture of 3-(4-methoxybenzenethio)-propylmalonic acid, diethyl ester (2.4 g, 7.0 mmol) in chloroform (150 mL) is cooled and m-chloroperoxybenzoic acid (3.3 g, 15 mmol) is added in small portions. After stirring overnight at ambient temperature, the mixture is transferred to chloroform/methyl alcohol (9/1) and extracted with aqueous sodium bicarbonate, brine, and concentrated in vacuo. The concentrate is chromatographed over silica gel using chloroform/methyl alcohol (99.5/0.5), and the eluate concentrated in vacuo to yield the title compound as a clear, colorless oil.

$^1$H NMR (DMSO) δ 7.77, 7.14, 4.06, 3.84, 3.49, 3.26, 1.79, 1.51, 1.11; $^{13}$C NMR (DMSO) δ 169.16, 163.67, 130.92, 115.04, 61.36, 56.23, 54.84, 50.90, 27.03, 20.69, 14.32.

Step 3 Preparation of 3-(4-methoxybenzenesulfonyl)-propylmalonic acid, monoethyl ester.

To a stirred mixture of 3-(4-methoxybenzenesulfonyl)-propylmalonic acid, diethyl ester (2.0 g, 5.4 mmol) in absolute ethyl alcohol (50 mL) is added potassium hydroxide (0.41 g, 5.9 mmol) in absolute ethyl alcohol. After stirring overnight at ambient temperature, the mixture is partitioned between chloroform/methyl alcohol (9/1) and aqueous sodium hydroxide. The aqueous phase is acidified with concentrated hydrochloric acid, extracted with chloroform/methyl alcohol (9/1), and the organic extracts concentrated in vacuo to yield the title compound as a clear, colorless oil.

$^1$H NMR (DMSO) δ 7.18, 7.15, 4.06, 3.85, 3.36, 3.27, 1.80, 1.54, 1.13; $^{13}$C NMR (DMSO) δ 170.97, 169.99, 164.03, 131.32, 130.73, 61.54, 56.60, 55.33, 51.57, 27.53, 21.17, 14.73.

Step 4 Preparation of 2-[(4-methoxybenzenesulfonyl) propyl]-2-propenoic acid, ethyl ester.

A mixture of 3-(4-methoxybenzenesulfonyl)-propylmalonic acid, monoethyl ester (1.1 g, 3.2 mmol), paraformaldehyde (0.11 g, 3.5 mmol), piperidine (0.03 mL, 0.32 mmol), and pyridine (20 mL) is refluxed for three hours. The mixture is transferred to ethyl acetate and extracted with aqueous 10% hydrochloric acid, distilled water, aqueous sodium bicarbonate, brine, and the organic phase is concentrated in vacuo to yield the title compound as a clear, colorless oil.

$^1$H NMR (DMSO) δ 7.79, 7.15, 6.05, 5.59, 4.09, 3.84, 3.21, 2.29, 1.67, 1.16; $^{13}$C NMR (DMSO) δ 166.80, 164.05, 139.74, 131.30, 130.78, 126.72, 115.44, 61.17, 56.61, 55.23, 30.45, 22.33, 14.80.

Step 5 Preparation of 2-[(4-methoxybenzenethio)methyl]-5-(4 methoxybenzenesulfonyl)-pentanoic acid, ethyl ester.

To a stirred mixture of 4-methoxybenzenethiol (0.30 mL, 2.2 mmol) in absolute ethyl alcohol (1 mL) cooled in an ice bath, is added sodium ethoxide solution (0.2 mL, 0.22 mmol) followed in fifteen minutes by 2-[(4-methoxybenzenesulfonyl) propyl]-2-propenoic acid, ethyl ester (0.70 g, 2.2 mmol) in absolute ethyl alcohol (2 mL). After stirring overnight at ambient temperature, the mixture is transferred to ethyl acetate and extracted with aqueous 10% hydrochloric acid, distilled water, aqueous sodium bicarbonate, brine, dried over anhydrous sodium sulfate, and concentrated in vacuo. The concentrate is triturated with hexane, the filtered solids extracted with chloroform and concentrated in vacuo to yield the title compound as a white solid.

$^1$H NMR (DMSO) δ 7.76, 7.31, 7.14, 6.86, 3.96, 3.83, 3.72, 3.16, 2.90, 2.40, 1.58, 1.44, 1.08; $^{13}$C NMR (DMSO) δ 173.70, 163.70, 159.18, 133.49, 130.87, 125.42, 115.23, 115.04, 60.56, 56.23, 55.66, 55.00, 45.05, 37.08, 29.88, 20.81, 14.48.

Step 6 Preparation of 2-[(4-methoxybenzenesulfonyl) methyl]-5-(4-methoxybenzenesulfonyl)-pentanoic acid, ethyl ester.

To a stirred mixture of 2-[(4-methoxybenzenethio) methyl]-5-(4-methoxybenzenesulfonyl)-pentanoic acid, ethyl ester (0.8 g, 1.8 mmol) in chloroform (50 mL) cooled in an ice bath, is added m-chloroperoxybenzoic acid (0.81 g, 3.7 mmol). After stirring overnight at ambient temperature, the mixture is transferred to ethyl acetate which is extracted with aqueous sodium bicarbonate and brine. The organic phase is concentrated in vacuo, triturated with hexane, and the filtered solids dissolved in chloroform. The chloroform mixture is then extracted with aqueous sodium bicarbonate and brine and the organic phase is concentrated in vacuo to yield the title compound as a white solid.

$^1$H NMR (DMSO) δ 7.75, 7.15, 3.89, 3.85, 3.50, 3.39, 3.16, 2.59, 1.57, 1.42, 1.57, 1.41, 1.08; $^{13}$C NMR (DMSO) δ 172.94, 164.27, 164.06, 131.21, 130.95, 130.73, 115.46, 61.37, 57.29, 56.66, 56.62, 55.17, 30.78, 20.81, 14.65.

Step 7 Preparation of 2-[(4-methoxybenzenesulfonyl) methyl]-5-(4-methoxybenzenesulfonyl)-pentanoic acid.

A mixture of 2-[(4-methoxybenzenesulfonyl)methyl]-5-(4-methoxybenzenesulfonyl)-pentanoic acid, ethyl ester (0.70 g, 1.4 mmol) in 6N hydrochloric acid (20 ml) is refluxed overnight. The mixture is transferred to ethyl acetate which is extracted with aqueous sodium bicarbonate. The combined aqueous extract is acidified with concentrated hydrochloric acid and extracted with ethyl acetate. This organic extract is concentrated in vacuo to yield the title compound as a white solid.

$^1$H NMR (DMSO) δ 12.5, 7.77, 7.14, 3.85, 3.50, 3.32, 3.16, 2.49, 1.57, 1.45; $^{13}$C NMR (DMSO) δ 174.41, 164.20, 164.03, 131.29, 131.17, 130.90, 130.67, 115.45, 80.03, 57.24, 56.62, 55.28, 30.68, 20.73.

Step 8 Preparation of N-benzyloxy-2-[(4-methoxybenzenesulfonyl)methyl]-5-(4-methoxybenzenesulfonyl)-pentanamide.

A mixture of 2-[(4-methoxybenzenesulfonyl)methyl]-5-(4-methoxybenzenesulfonyl)-pentanoic acid (0.5 g, 1.1 mmol), benzylhydroxylamine hydrochloride (0.21 g, 1.3 mmol), 1-(3-dimethylaminopropyl)-3-ethylcarbodiimide hydrochloride (0.42 g, 2.2 mmol), and tetrahydrofuran/water (1/1, 10 mL) is stirred at ambient temperature overnight. The mixture is transferred to ethyl acetate which is extracted with aqueous 10% hydrochloric acid, distilled water, aqueous sodium bicarbonate, and brine. The organic phase is concentrated in vacuo to yield the title compound as a white solid.

$^1$H NMR (DMSO) δ 11.2, 7.76, 7.37, 7.12, 4.60, 3.84, 3.78, 3.50, 3.22, 3.10, 2.39, 1.48, 1.35.

Step 9 Preparation of N-hydroxy-2-[(4-methoxybenzenesulfonyl)methyl]-5-(4-methoxybenzenesulfonyl)-pentanamide.

A mixture of N-benzyloxy-2-[(4-methoxybenzenesulfonyl)methyl]-5-(4-methoxybenzenesulfonyl)-pentanamide (0.3 g, 0.5 mmol), Pearlman's catalyst (0.11 g), and absolute ethyl alcohol is agitated under hydrogen (15 psig) overnight at room temperature. The mixture is filtered and the filtrate is concentrated in vacuo. The concentrate is chromatographed over silica gel with chloroform/ethyl acetate/methyl alcohol/acetic acid (50/40/10/1) and the eluate concentrated in vacuo to afford the title compound as a white solid.

IR (mull) 1667, 1596, 1578, 1499, 1317, 1294, 1263, 1141, 1089, 1024, 837, cm$^{-1}$; MS (FAB) m/z 473, 472, 391, 371, 149, 129, 71, 57, 55, 43; Specific Rotation [α]$^{25}_D$=0; $^1$H NMR (DMSO) δ 10.5, 8.8, 7.76, 7.14, 3.86, 3.42, 3.18, 2.3, 1.46.

EXAMPLE 12

Preparation of N-hydroxy-2-(n-octylsulfonylmethyl)-3-(4-methoxybenzenesulfonyl)-propionamide.

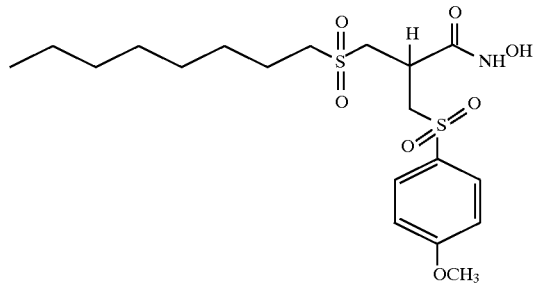

Step 1 Preparation of 2-[(n-octylthio)methyl]-2-propenoic acid.

A mixture of 2-bromomethylacrylic acid (1.0 g, 6.0 mmol), n-octylthiol (1.2 mL, 6.6 mmol), and dimethylformamide (10 mL) is refluxed overnight. The mixture is then transferred to ethyl acetate and extracted with aqueous 10% hydrochloric acid and distilled water. The organic phase is concentrated in vacuo to afford the title compound as a white solid.

$^1$H NMR (DMSO) δ 6.00, 5.60, 3.27, 2.37, 1.46, 1.28, 1.22, 0.84; $^{13}$C NMR (DMSO) δ 167.62, 138.23, 125.42, 32.28, 31.69, 31.07, 29.15, 29.06, 29.02, 28.70, 22.53, 14.37.

Step 2 Preparation of 2-[(n-octylthio)methyl]-3-(4-methoxybenzenethio)-propenoic acid.

A mixture of 2-[(n-octylthio)methyl]-2-propenoic acid (1.0 g, 4.3 mmol), 4-methoxybenzenethiol (1.1 mL, 8.6 mmol), and dimethylformamide (25 mL) is refluxed overnight. The mixture is partitioned between ethyl acetate and aqueous 10% hydrochloric acid and the organic phase is concentrated in vacuo. The concentrate is chromatographed over silica gel using chloroform/methyl alcohol/acetic acid (98/1/1) and the eluate is concentrated in vacuo to yield the title compound as a white solid.

$^1$H NMR (DMSO) δ 12.5, 7.36, 6.90, 3.73, 3.04, 2.72, 2.55, 2.38, 1.42, 1.21, 0.84; $^{13}$C NMR (DMSO) δ 174.76, 159.53, 133.66, 152.92, 152.65, 115.58, 55.98, 46.02, 36.80, 33.12, 32.28, 32.07, 29.87, 29.55, 29.47, 29.39, 22.93, 14.75.

Step 3 Preparation of 2-[(n-octylsulfonyl)methyl]-3-(4-methoxybenzenesulfonyl)propionic acid.

To a stirred mixture of 2-[(n-octylthio)methyl]-3-(4-methoxybenzenethio)-propionoic acid (0.6 g, 1.6 mmol) in chloroform (15 mL) cooled in an ice bath, is added m-chloroperoxybenzoic acid (1.4 g, 6.6 mmol). After stirring at ambient temperature overnight, the mixture is partitioned between hexane and aqueous 10% hydrochloric acid and the aqueous phase is further extracted with hexane and with ethyl acetate. The ethyl acetate extract is concentrated in vacuo and chromatographed over silica gel with chloroform/methyl alcohol/acetic acid (98/1/1) to yield the title compound as a white solid.

$^1$H NMR (DMSO) δ 7.80, 7.17, 3.68, 3.61, 3.49, 3.38, 3.02, 1.59, 1.32, 1.23, 0.85.

Step 4 Preparation of N-hydroxy-2-[(n-octylsulfonyl)methyl]-3-(4-methoxybenzenesulfonyl)-propionamide.

Following the general procedure outlined in EXAMPLE 4 (steps 3 and 4) and making non-critical variations but starting with 2-[(n-octylsulfonyl)methyl]-3-(4-methoxybenzenesulfonyl)-propionic acid (0.5 g, 1.2 mmol) in step 3, the title compound is obtained as a white solid.

m.p. 134.5° C.; MS (FAB) m/z 451, 450, 434, 239, 133, 57, 43, 41, 39; $^1$H NMR (DMSO) δ 10.9, 8.9, 7.80, 7.15, 3.86, 3.73, 3.50, 3.01, 2.70, 2.36, 1.55, 1.08, 0.82; $^{13}$C NMR (DMSO) δ 166.20, 163.90, 130.82, 130.58, 115.13, 60.87, 56.27, 52.90, 52.68, 44.69, 32.98, 31.63, 28.87, 28.13, 22.51, 21.63, 14.40.

EXAMPLE 13

Preparation of N-hydroxy-2-[methyl-3-(1-methylhydantoin)]-3-(4-methoxybenzenesulfonyl)l-propionamide.

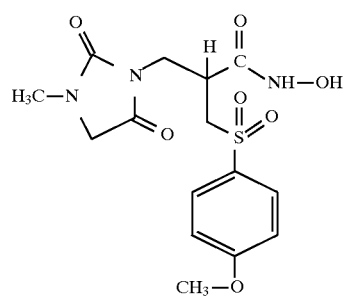

Step 1 Preparation of 2-[methyl-3-(1-methylhydantoin)]-2-propenoic acid.

A mixture of 2-bromomethylacrylic acid (1.0 g, 6.0 mmol), 1-methylhydantoin (0.85 g, 7.2 mmol), sodium bicarbonate (1.1 g, 13 mmol), and toluene (50 mL) is refluxed overnight. The mixture is transferred to ethyl acetate and extracted with aqueous sodium bicarbonate. The aqueous phase is acidified with concentrated hydrochloric acid and extracted with ethyl acetate and chloroform/methyl alcohol (9/1). Concentration of the organic extracts yields the title compound as a solid.

$^1$H NMR (DMSO) δ 6.08, 5.47, 4.08, 4.00, 2.85.

Step 2 Preparation of 2-[methyl-3-(1-methylhydantoin)]-3-(4-methoxybenzenethio)-propionic acid.

A mixture of 2-methenyl-2-[methyl-3-(1-methylhydantoin)]-propenoic acid (1.1 g, 5.5 mmol), 4-methoxybenzenethiol (0.75 mL, 6.0 mmol), sodium bicarbonate (0.92 g, 11 mmol), and toluene (50 mL) is refluxed overnight. The mixture is concentrated in vacuo and chromatographed over silica gel using chloroform/methyl alcohol/acetic acid (97/2/1). The eluate is concentrated in vacuo and triturated with hexane to yield the title compound as a white solid.

$^1$H NMR (DMSO) δ 12.3, 7.33, 6.90, 3.92, 3.74, 3.60, 2.95, 2.83, 2.74; $^{13}$C NMR (DMSO) δ 173.90, 171.02, 159.58, 156.98, 133.87, 152.92, 115.61, 56.02, 62.01, 44.45, 40.13, 35.63, 30.01.

Step 3 Preparation of 2-[methyl-3-(1-methylhydantoin)]-3-(4-methoxybenzenesulfonyl)-propionic acid.

A mixture of 2-[methyl-3-(1-methylhydantoin)]-3-(4-methoxybenzenethio)-propionoic acid (1.0 g, 3.0 mmol) in methylene chloride (50 mL) is cooled and m-chloroperoxybenzoic acid (1.4 g, 6.3 mmol) is added. After stirring at ambient temperature overnight, the mixture is concentrated in vacuo and chromatographed over silica gel 60 (230–400 mesh) using chloroform/methyl alcohol/acetic acid (94/5/1). The eluate is concentrated in vacuo to yield the title compound as a white solid.

$^1$H NMR (DMSO) δ 7.75, 7.14, 3.87, 3.84, 3.54, 3.35, 2.92, 2.80.

Step 4 Preparation of N-hydroxy-2-[methyl-3-(1-methylhydantoin)]-3-(4-methoxybenzenesulfonyl)-propionamide.

Following the general procedure outlined in EXAMPLE 4 (steps 3 and 4) and making non-critical variations but starting with 2-[methyl-3-(1-methylhydantoin)]-3-(4-methoxybenzenesulfonyl)-propionoic acid (0.6 g, 1.6 mmol) in step 3 the title compound is obtained.

MS (EI) m/z 385 (M+), 214, 181, 172, 171, 155, 123, 107, 99, 77, 56; $^1$H NMR (DMSO) δ 10.8, 8.2, 7.76, 7.13, 3.84, 3.44, 3.24, 2.81; $^{13}$C NMR (DMSO) δ 170.68, 166.39, 163.77, 156.41, 130.72, 130.51, 115.06, 56.26, 54.99, 51.68, 39.68, 37.24, 29.66.

EXAMPLE 14
Preparation of N-hydroxy-2-[methyl-3-(1-butylhydantoin)]-3-(4-butoxybenzenesulfonyl)-propionamide.

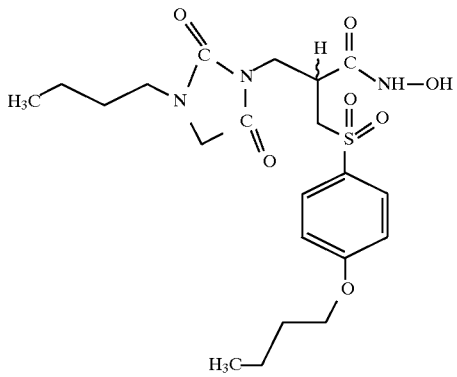

Step 1 Preparation of 4-butoxybenzenesulfinic acid, sodium salt.

To a stirred mixture of sodium iodide (8.8 g, 59 mmol) in acetone (250 mL) is added 4-butoxybenzenesulfonyl chloride (5.0 g, 20 mmol). After stirring at ambient temperature overnight, the mixture is filtered and the filtered solids washed with acetone to afford 4-butoxybenzenesulfinic acid, sodium salt as a white solid.

$^1$H NMR (DMSO) δ 7.49, 6.81, 3.93, 1.67, 1.40, 0.90.

Step 2 Preparation of 2-[(4-butoxybenzenesulfonyl)methyl]-2-propenoic acid.

A mixture of 2-bromomethylacrylic acid (1.0 g, 6.0 mmol), 4-butoxybenzenesulfinic acid, sodium salt (3.1 g, 13 mmol), sodium carbonate (1.9 g, 18 mmol) and dimethylformamide (20 mL) is refluxed overnight. The reaction mixture is then partitioned between ethyl acetate and aqueous 10% hydrochloric acid and the organic phase is concentrated in vacuo. The concentrate is chromatographed over silica gel 60 (230–400 mesh) with chloroform/methyl alcohol/acetic acid (94/5/1) and the eluate concentrated in vacuo to afford the title compound as a white solid.

$^1$H NMR (DMSO) δ 12.9, 7.67, 7.10, 6.28, 5.70, 4.22, 4.03, 1.68, 1.41, 0.90; $^{13}$C NMR (DMSO) δ 167.04, 163.63, 133.06, 131.33, 130.91, 130.47, 114.08, 68.69, 57.60, 31.33, 19.48, 14.47.

Step 3 Preparation of 2-[methyl-3-(1-butylhydantoin)]-3-(4-butoxybenzenesulfonyl)-propionoic acid.

A mixture of 2-[(4-butoxybenzenesulfonyl)methyl]-2-propenoic acid (1.0 g, 3.4 mmol), 1-butylhydantoin (0.78 g, 5.0 mmol), sodium bicarbonate (0.63 g, 7.4 mmol), and toluene (50 mL) is refluxed overnight. The reaction mixture is transferred to ethyl acetate, extracted with aqueous 10% hydrochloric acid, and concentrated in vacuo. The concentrate is triturated with hexane and diethyl ether to yield the title compound as a white solid.

$^1$H NMR (DMSO) δ 7.73, 7.14, 5.74, 4.07, 3.90, 3.59, 3.54, 3.23, 2.95, 1.72, 1.42, 1.24, 0.93, 0.87; $^{13}$C NMR (DMSO) δ 172.46, 171.21, 163.73, 156.53, 130.89, 130.63, 115.88, 68.73, 55.72, 55.52, 49.94, 42.42, 31.32, 29.83, 20.02, 19.47, 14.47, 14.34.

Step 4 Preparation of N-hydroxy-2-[methyl-3-(1-butylhydantoin)]-3-(4-butoxybenzenesulfonyl)-propionamide.

Following the general procedure outlined in EXAMPLE 4 (steps 3 and 4) and making non-critical variations but starting with 2-[methyl-3-(1-butylhydantoin)]-3-(4-butoxybenzenesulfonyl)-propionoic acid (0.59 g, 1.3 mmol) in step 3 the title compound is obtained as a white solid.

MS (FAB) m/z 471, 470, 469, 223, 197, 149, 57, 41, 23; $^1$H NMR (DMSO) δ 10.8, 8.8, 7.74, 7.10, 5.73, 4.06, 3.88, 3.47, 3.21, 2.82, 1.71, 1.42, 1.25, 0.92, 0.87.

EXAMPLE 15

Preparation of N-hydroxy-2-[methyl-3-(1-butylhydantoin)]-3-(4-methoxybenzenesulfonyl)-propionamide.

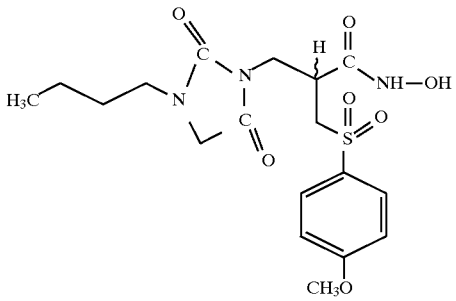

Following the general procedure outlined in EXAMPLE 14 (steps 1 to 4) and making non-critical variations but starting with 4-methoxybenzenesulfonyl chloride in step 1, the title compound is obtained as a white solid.

MS (FAB) m/z 428 (MH+), 429, 428, 223, 149, 129, 71, 57, 55, 43, 41; $^1$H NMR (DMSO) δ 10.80, 8.81, 7.77, 7.12, 3.85, 3.49, 3.23, 2.83, 1.43, 1.24, 0.88; $^{13}$C NMR (DMSO) δ 170.79, 166.40, 163.77, 156.17, 130.78, 130.47, 115.08, 55.26, 55.08, 46.63, 42.10, 41.2, 37.25, 29.49, 19.68, 13.99.

EXAMPLE 16

Preparation of N-hydroxy-2-[methyl-3-(5,5-dimethylhydantoin)]-3-(4-methoxybenzenesulfonyl)-propionamide.

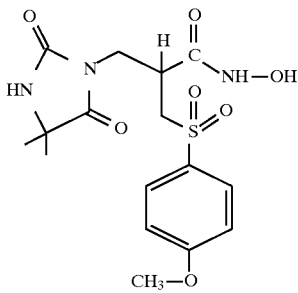

Following the general procedure outlined in EXAMPLE 14 (steps 1 to 4) and making non-critical variations but starting with 5,5-dimethylhydantoin (1.5 g, 11 mmol) in step 3, the title compound is obtained as a white solid.

$^1$H NMR (DMSO) δ 10.8, 8.2, 7.77, 7.12, 3.84, 3.41, 3.17, 2.85, 1.21; $^{13}$C NMR (DMSO) δ 177.62, 166.35, 163.82, 155.28, 130.85, 130.49, 115.14, 58.16, 56.26, 55.37, 37.20, 24.95, 24.87.

EXAMPLE 17

Preparation of (+)-N-hydroxy-2-[(n-octylsulfonyl)methyl]-3-(4-methoxybenzenesulfonyl)-propionamide and (−)-N-hydroxy-2-[(n-octylsulfonyl)methyl]-3-(4-methoxybenzenesulfonyl) propionamide.

A racemic mixture of N-hydroxy-2-[(4-methoxybenzenesulfonyl)methyl]-3-(n-octylsulfonyl) propionamide (EXAMPLE 12) is eluted over a Chiralpak AD, column with absolute ethyl alcohol and the eluates collected at $R_f$=13.5 minutes and $R_f$=23.5 minutes are concentrated in vacuo to yield an enantiomer (17A) ($[\alpha]^{25}_D$=+4°) and an enantiomer (17B) ($[\alpha]^{25}_D$=−4°), respectively.

EXAMPLE 18

Preparation of (+)-N-hydroxy-2-[methyl-3-(1-methylhydantoin)]-3-(4-methoxybenzenesulfonyl)-propionamide and (−)-N-hydroxy-2-[methyl-3-(1-methylhydantoin)]-3-(4-methoxybenzenesulfonyl)-propionamide.

A racemic mixture of N-hydroxy-2-[methyl-3-(1-methylhydantoin)]-3-(4-methoxybenzenesulfonyl)-propionamide (EXAMPLE 13) is eluted over a Chiralpak AD, column with absolute ethyl alcohol and the eluates collected at $R_f$=8.6 minutes and $R_f$=10.5 minutes are concentrated in vacuo to yield the enantiomers, 18A and 18B, respectively.

EXAMPLE 19

Preparation of (+)-N-hydroxy-2-[methyl-3-(1-butylhydantoin)]-3-(4-butoxybenzenesulfonyl)-propionamide and (−)-N-hydroxy-2-[methyl-3-(1-butylhydantoin)]-3-(4-butoxybenzenesulfonyl)-propionamide.

A racemic mixture of N-hydroxy-2-[methyl-3-(1-butylhydantoin)]-3-(4-butoxybenzenesulfonyl)-propionamide (EXAMPLE 14) is eluted over a Chiralpak AD column with absolute ethyl alcohol and the eluates collected at $R_f$=16.5 minutes and $R_f$=17.8 minutes are concentrated in vacuo to yield an enantiomer (19A) ($[\alpha]^{25}_D$=−3°) and an enantiomer (19B) ($[\alpha]^{25}_D$=+3°), respectively.

EXAMPLE 20

Preparation of (+)-N-hydroxy-2-[methyl-3-(1-butylhydantoin)]-3-(4-methoxybenzenesulfonyl)-propionamide and (−)-N-hydroxy-2-[methyl-3-(1-butylhydantoin)]-3-(4-methoxybenzenesulfonyl)-propionamide.

A racemic mixture of N-hydroxy-2-[methyl-3-(1-butylhydantoin)]-3-(4-methoxybenzenesulfonyl)-propionamide (EXAMPLE 15) is eluted over a Chiralpak AD column with absolute ethyl alcohol and the eluates collected at $R_f$=13.4 minutes and $R_f$=15.8 minutes are concentrated in vacuo to yield an enantiomer (20A) ($[\alpha]^{25}_D$=−4°) and an enantiomer (20B) ($[\alpha]^{25}_D$=+4°), respectively.

EXAMPLE 21

Biological Activity Test

Inhibitory activity is evaluated in one or more of the MMP enzymes (stromelysin, gelatinase, and collagenase) in vitro using particle concentration fluorescence assay. An inhibitor binds to MMP enzymes which prevents the degradation of a substrate by stromelysin, gelatinase, or collagenase. The substrate has attached to it a fluorescein and a biotin moiety. The intact substrate then binds to an avidin-coated particle via the biotin moiety. Once the particle is washed and dried, a fluorescent signal is generated since the fluorescent group is attached to the particle. Without an inhibitor present, the substrate is degraded by MMP enzymes and the fluorescein group is removed, therefore, no fluorescent signal can be detected. Testing compounds are dissolved in DMSO to the desired concentration, then the solutions are diluted to 1:5 with MMP buffer (50 mM Tris-HCl, pH 7.5; 150 mM NaCl; 0.02% $NaN_3$). Serial two-fold dilutions of each compound are prepared. A concentrated, activated enzyme solution is transferred into each plate of the testing compounds, and the mixture is incubated at room temperature for 15 minutes. Thawed MMP substrate is then added into all plates, and the plates are incubated in the dark for 1–3 hours at room temperature. At this point, the substrate mixture is mixed with 0.1% avidin-coated polystyrene particles. After 15 minutes, the fluorescence values are measured following filtration and washing of the beads. Ki values are then calculated. Inhibitory data for the compounds of this invention are shown in TABLE 1. Compounds with lower Ki values are expected to be more effective as MMP inhibitors. It is expected that a compound with a Ki less than 15 $\mu$M against stromelysin will display therapeutic effects in connective tissue disorders.

TABLE 1

MMP Inhibition Constants (Ki, $\mu$M) of the Compounds of the Invention

| Example No. | Stromelysin Ki ($\mu$M) | Gelatinase Ki ($\mu$M) |
|---|---|---|
| 1 | 0.049 | 0.0092 |
| 2 | 1.1 | 0.087 |
| 3 | 3.6 | 0.081 |
| 4 | 0.0039 | 0.00019 |
| 5 | 0.072 | 0.0019 |
| 6 | 0.092 | 0.0025 |
| 7 | 1 | 0.35 |
| 8 | 0.44 | 0.19 |
| 9 | 0.13 | 0.0038 |
| 10 | 0.16 | 0.008 |
| 11 | 0.001 | 0.001 |
| 12 | 0.0054 | 0.00082 |
| 13 | 0.017 | 0.0013 |
| 14 | 0.0018 | 0.000092 |
| 15 | 0.009 | 0.00034 |

SCHEME I

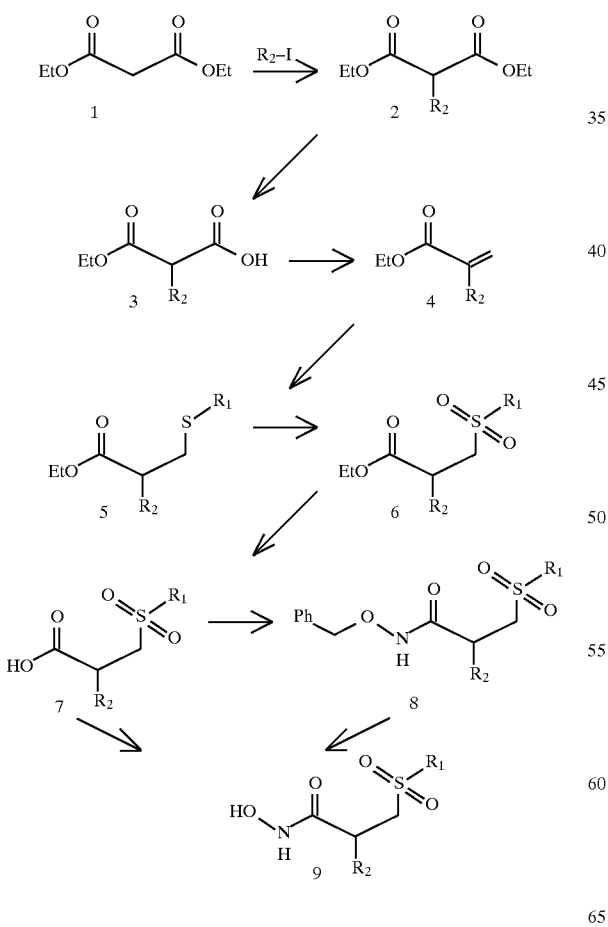

SCHEME II

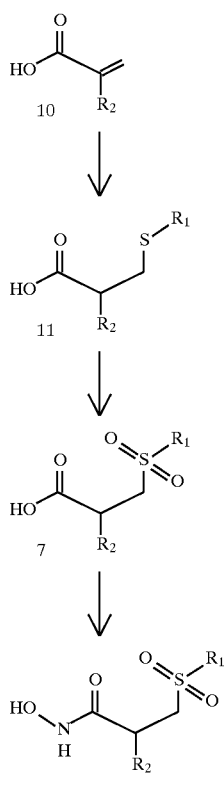

SCHEME III

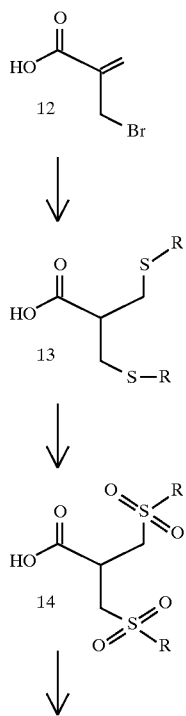

SCHEME III -continued

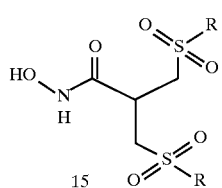
15

SCHEME IV

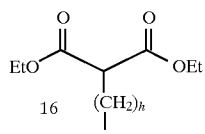
16

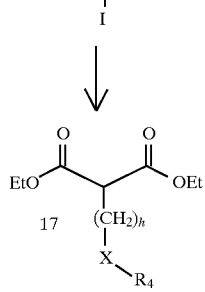
17

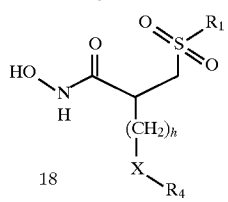
18

SCHEME V

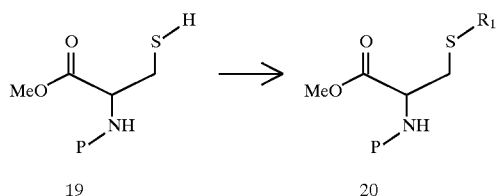
19　　20

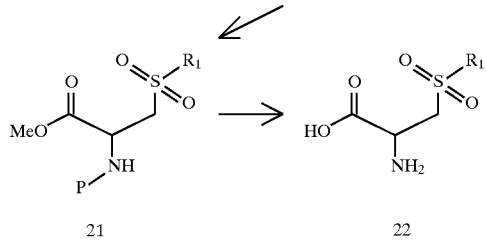
21　　22

SCHEME V -continued

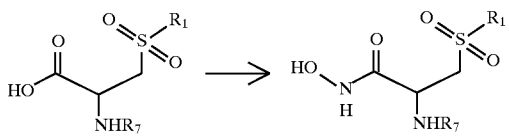
23　　24

SCHEME VI

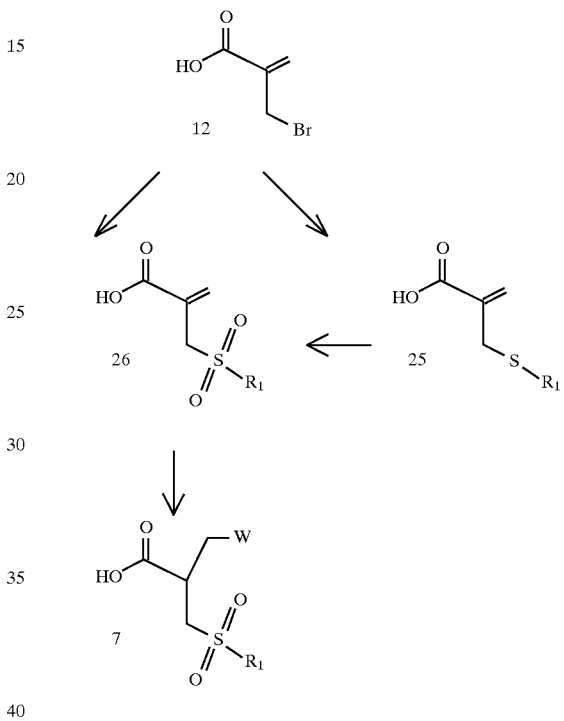

We claim:

1. A compound of formula I

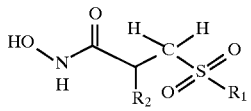

or pharmaceutical acceptable salts thereof wherein:

$R_1$ is
 a) $C_{4-12}$ alkyl,
 b) $C_{4-12}$ alkenyl,
 c) $C_{4-12}$ alkynyl,
 d) —$(CH_2)_n$-$C_{3-8}$ cycloalkyl,
 e) —$(CH_2)_n$-aryl,
 f) —$(CH_2)_n$-aryl substituted with $C_{1-4}$ alkyl, $C_{1-4}$ alkoxy, halo, —$NO_2$, —$CF_3$, —CN, or —N($C_{1-4}$ alkyl)$_2$,
 g) —$(CH_2)_n$-het, or
 h) —$(CH_2)_n$-het substituted with $C_{1-4}$ alkyl, or halo;

$R_2$ is
 a) $C_{1-12}$ alkyl,
 b) $C_{1-12}$ alkyl substituted with one to three halo, —CN, —$NO_2$, —$CF_3$, —N($R_3$)$_2$, —$SR_3$, or OH,
 c) $C_{2-12}$ alkenyl,
 d) $C_{2-12}$ alkenyl substituted with one to three halo, —CN, —$NO_2$, or —$CF_3$, e) $C_{2-12}$ alkynyl,
f) $C_{2-12}$ alkynyl substituted with one to three halo, —CN, —NO$_2$, or —CF$_3$,
g) —(CH$_2$)$_h$-C$_{3-8}$ cycloalkyl,
h) —(CH$_2$)$_h$-C$_{3-8}$ cycloalkyl substituted with one to three $C_{1-4}$ alkyl, $C_{1-4}$ alkoxy, or halo,
i) —(CH$_2$)$_h$-C$_{3-8}$ cycloalkenyl,
j) —(CH$_2$)$_h$-C$_{3-8}$ cycloalkenyl substituted with one to three $C_{1-4}$ alkyl, $C_{1-4}$ alkoxy, or halo,
k) —(CH$_2$)$_h$-aryl,
l) —(CH$_2$)$_h$-aryl substituted with one to three $C_{1-4}$ alkyl, $C_{1-4}$ alkoxy, —CF$_3$—OH, —NO$_2$, —CN, —N(R$_3$)$_2$, —SR$_3$, —SO$_2$(C$_{1-4}$ alkoxy), —C(=O)R$_3$, or —NC(=O)R$_3$,
m) —(CH$_2$)$_h$-aryl substituted with one to five halo,
n) —(CH$_2$)$_h$-het,
o) —(CH$_2$)$_h$-het substituted with one to two $C_{1-4}$ alkyl, or halo,
p) —(CH$_2$)$_h$-Q,
q) —(CH$_2$)$_h$-Q substituted with one to three $C_{1-4}$ alkyl, $C_{1-4}$ alkoxy, halo, or phenyl,
r) —(CH$_2$)$_i$-X-R$_4$, optionally the —(CH$_2$)$_i$- chain can be substituted with $C_{1-4}$ alkyl or phenyl, which in turn can be substituted with one to three halo or $C_{1-4}$ alkyl, or
s) —(CH$_2$)$_i$CHR$_5$R$_6$;

R$_3$ is
a) H,
b) $C_{1-4}$ alkyl,
c) —(CH$_2$)$_h$-phenyl, or
d) —(CH$_2$)$_h$-phenyl substituted with one to three $C_{1-4}$ alkyl, $C_{1-4}$ alkoxy, or halo;

X is
a) —O—,
b) —S(=O)$_j$-,
c) —NR$_7$-,
d) —S(=O)$_2$NR$_8$-, or
e) —C(=O)—;

R$_4$ is
a) H,
b) $C_{1-4}$ alkyl,
c) —(CH$_2$)$_h$-phenyl,
d) —(CH$_2$)$_h$-phenyl substituted with one to three $C_{1-4}$ alkyl, $C_{1-4}$ alkoxy, halo, —NO$_2$, or —CN, or
e) —(CH$_2$)$_h$-het;

R$_5$ is
a) $C_{1-4}$ alkyl, or
b) —C(=O)R$_3$;

R$_6$ is
a) —C(=O)R$_3$, or
b) —(CH$_2$)$_h$C(=O)R$_3$;

R$_7$ is
a) H,
b) $C_{1-4}$ alkyl,
c) —(CH$_2$)$_h$-phenyl,
d) —(CH$_2$)$_h$-phenyl substituted with one to three $C_{1-4}$ alkyl, $C_{1-4}$ alkoxy, or halo,
e) —C(=O)—R$_3$,
f) —S(=O)$_2$R$_3$, or
g) —C(=O)OR$_3$;

R$_8$ is
a) $C_{1-4}$ alkyl,
b) —(CH$_2$)$_h$-phenyl, or
c) —(CH$_2$)$_h$-phenyl substituted with one to three $C_{1-4}$ alkyl, $C_{1-4}$ alkoxy, or halo;

aryl is monocarbocyclic, or bicarbocyclic aromatic moiety;

het is 5- to 10-membered unsaturated heterocyclic moiety having one to three atoms selected from the group consisting of oxygen, nitrogen, and sulfur;

Q is 5- to 10-membered saturated heterocyclic moiety having one to two atoms selected from the group consisting of oxygen, nitrogen, and sulfur;

h is 0, 1, 2, 3, 4, 5, or 6;
i is 0, 1, 2, 3, 4, 5, 6, 7, 8, 9, or 10; and
j is 0, 1, or 2.

2. A compound of formula I according to claim 1 wherein R$_2$ is
a) $C_{1-12}$ alkyl substituted with one to three halo, —CN, —NO$_2$, —CF$_3$, —N(R$_3$)$_2$, —SR$_3$, or OH,
b) $C_{2-12}$ alkenyl,
c) $C_{2-12}$ alkenyl substituted with one to three halo, —CN, —NO$_2$, or —CF$_3$,
d) $C_{2-12}$ alkynyl,
e) $C_{2-12}$ alkynyl substituted with one to three halo, —CN, —NO$_2$, or —CF$_3$,
f) —(CH$_2$)$_h$-C$_{3-8}$ cycloalkyl substituted with one to three $C_{1-4}$ alkyl, $C_{1-4}$ alkoxy, or halo,
g) —(CH$_2$)$_h$-C$_{3-8}$ cycloalkenyl,
h) —(CH$_2$)$_h$-C$_{3-8}$ cycloalkenyl substituted with one to three $C_{1-4}$ alkyl, $C_{1-4}$ alkoxy, or halo,
i) aryl,
j) aryl substituted with one to three $C_{1-4}$ alkyl, $C_{1-4}$ alkoxy, —CF$_3$ —OH, —NO$_2$, —CN, —N(R$_3$)$_2$, —SR$_3$,—SO$_2$(C$_{1-4}$ alkoxy), —C(=O)R$_3$, or —NC(=O)R$_3$,
k) —(CH$_2$)$_h$-het,
l) —(CH$_2$)$_h$-het substituted with one to two $C_{1-4}$ alkyl, or halo,
m) —(CH$_2$)$_i$-Q,
n) —(CH$_2$)$_i$-Q substituted with one to three $C_{1-4}$ alkyl, $C_{1-4}$ alkoxy, halo, or phenyl,
o) —(CH$_2$)$_i$-X-R$_4$, optionally the —(CH$_2$)$_i$- chain can be substituted with $C_{1-4}$ alkyl or phenyl, which in turn can be substituted with one to three halo or $C_{1-4}$ alkyl, or
p) —(CH$_2$)$_h$CHR$_5$R$_6$;

wherein R$_3$, X, R$_4$, R$_5$, R$_6$, R$_7$, R$_8$, aryl, het and Q are as defined as in claim 1;
h is 0, 1, 2, 3, 4, 5, or 6; and
i is 1, 2, 3, 4, 5 or 6.

3. A compound of formula I according to claim 1 wherein R$_2$ is
a) —(CH$_2$)$_h$-het,
b) —(CH$_2$)$_h$-het substituted with one to two $C_{1-4}$ alkyl, or halo,
c) —(CH$_2$)$_i$-Q,
d) —(CH$_2$)$_i$-Q substituted with one to three $C_{1-4}$ alkyl, $C_{1-4}$ alkoxy, halo, or phenyl, or
e) —(CH$_2$)$_i$-X-R$_4$, optionally the —(CH$_2$)$_i$- chain can be substituted with $C_{1-4}$ alkyl or phenyl, which in turn can be substituted with one to three halo or $C_{1-4}$ alkyl;

wherein X, R$_4$, R$_7$, R$_8$, aryl, het and Q are as defined as in claim 1;
h is 0, 1, 2, 3, 4, 5, or 6; and
i is 1, 2, 3, 4, 5 or 6.

4. A compound of formula I according to claim 1 wherein R$_1$ is
a) $C_{4-8}$ alkyl, b) —(CH$_2$)$_h$-phenyl, or
c) —(CH$_2$)$_h$-phenyl substituted with C$_{1-4}$ alkyl, C$_{1-4}$ alkoxy, fluoro, chloro, or bromo;

R$_2$ is
  a) —(CH$_2$)$_h$-pyridyl, quinolinyl, pyrrolyl, thienyl, or thiazolyl, or indolyl, which can optionally be substituted with one to three C$_{1-4}$ alkyl, C$_{1-4}$ alkoxy, phenyl, fluoro, chloro, or bromo;
  b) —(CH$_2$)$_h$-piperdinyl, piperazinyl, morpholino, 4-thiomorpholinyl, butyrolactamyl, 2-oxo-oxazolidinyl, or 2,4-dioxo-imidazolidinyl, which can optionally be substituted with one to three C$_{1-4}$ alkyl, phenyl, fluoro, chloro, or bromo;
  c) —(CH$_2$)$_i$-X-R$_4$;

X is
  a) —S(=O)$_j$—,

R$_4$ is
  a) C$_{1-8}$ alkyl,
  b) phenyl, or
  c) phenyl substituted with C$_{1-4}$ alkyl, C$_{1-4}$ alkoxy, or halo;

h is 0, 1, 2, 3, 4, 5 or 6;
i is 1, 2, 3, 4, 5 or 6; and
j is 0, 1 or 2.

5. A compound of claim 1 wherein R$_1$ is selected from the group consisting of n-butyl, isobutyl, 1-methylpropyl, tert-butyl, n-pentyl, 3-methybutyl, n-hexyl, n-heptyl, n-octyl, phenyl, 4-methylphenyl, 4-ethylphenyl, 4-tert-butylphenyl, 4-chlorophenyl, 4-isopropylphenyl, 4-bromophenyl, 4-fluorophenyl, 4-trifluoromethylphenyl, 4-methoxyphenyl, 4-ethoxyphenyl, 4-n-butoxyphenyl, benzyl, 4-phenylbenzyl, 2-, 3-, or 4-fluorobenzyl, 2-, 3-, 4-chlorobenzyl, 2-, 3-, 4-bromobenzyl, and 4-ethoxybenzyl.

6. A compound of claim 1 wherein R$_1$ is selected from the group consisting of n-butyl, n-pentyl, n-hexyl, n-heptyl, n-octyl, phenyl, 4-methylphenyl, 4-ethylphenyl, 4-chlorophenyl, 4-bromophenyl, 4-fluorophenyl, 4-methoxyphenyl, 4-n-butoxyphenyl, benzyl, 4-fluorobenzyl, 4-chlorobenzyl, 4-bromobenzyl, and 4-ethoxybenzyl.

7. A compound of claim 1 wherein R$_2$ is selected from the group consisting of methyl, 1-cyano-1-phenyl methyl, 2-cyano ethyl, 2-phenylethyl, 2-bromo-2-phenylethyl, 2-bromoethyl, propyl, isopropyl, 3-chloropropyl, 3-bromopropyl, n-butyl, isobutyl, 3-methylbutyl, 1-methylpropyl, tert-butyl, n-pentyl, 3-methybutyl, n-hexyl, n-heptyl, n-octyl, n-hexadecyl, n-octadecyl, 2-propenyl, 2-propynyl, 3-butenyl, 4-pentenyl, 3-butenynyl, 4-pentenynyl, cyclopentyl, cyclohexyl, cyclohexylmethyl, 2-cyclohexylethyl, 4-cyclohexylbutyl, dimethylaminoethyl, dimethylaminopropyl, diethylaminopropyl, phenylaminomethyl, phenyl, 4-methylphenyl, 4-chlorophenyl, 4-bromophenyl, 4-fluorophenyl, 4-trifluoromethylphenyl, 2-methoxyphenyl, 4-methoxyphenyl, 4-nitrophenyl, 4-ethoxyphenyl, benzyl, 4-methylbenzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, and 2-methylbenzyl, 3-methylbenzyl, 4-methylbenzyl, 4-ethoxybenzyl, 4-nitrobenzyl, methylcarbonyl, 1-methylcarbonyl methyl, 2-phenylcarbonyl ethyl, isopropylcarbonyl, methoxycarbonyl, ethoxycarbonyl, 1,1-ethoxycarbonyl methyl, 2,2-ethoxycarbonyl ethyl, 1,2-ethoxycarbonyl ethyl, 2-methoxycarbonyl propyl, 3-methoxycarbonyl propyl, 1-ethoxycarbonyl methyl, 1-ethoxycarbonyl ethyl, phenylcarbonyl, phenylcarbonyl methyl, pyridylcarbonyl methyl, pyridylmethyl, pyridylethyl, quinolinylmethyl, pyrrolyl methyl, indolyl methyl, thienyl, thiazolyl, thienylmethyl, thienylethyl, piperdinyl methyl, piperazinyl methyl, morpholino methyl, morpholino ethyl, morpholino propyl, thiomorpholino methyl, thiomorpholino propyl, 4-methoxybenzenesulfonyl methyl, 3-(4-methoxybenzenesulfonyl)amino propyl, 3-hydroxy, amino, 3-phenoxy propyl, 2-phenyl ethyloxy, (4-butoxybenzenesulfonyl)methyl, methyl-3-(1,5,5-trimethylhydantoin), methyl-3-(1-butyl-5,5-dimethylhydantoin), (4-methoxybenzenesulfonyl)methyl, (4-chlorobenzenesulfonyl)-methyl, (4-bromobenzenesulfonyl)methyl, (n-butylsulfonyl)methyl, (n-octylsulfonyl)-methyl, 3-(4-methoxybenzenesulfonyl) propyl, (4-methylbenzenesulfonyl)methyl, (benzenesulfonyl)methyl, methyl-3-(1-methylhydantoin), methyl-3-(1-butylhydantoin) and methyl-3-(5,5-dimethylhydantoin).

8. A compound of claim 1 wherein R$_2$ is selected from the group consisting of (4-methoxybenzenesulfonyl)methyl, (4-chlorobenzenesulfonyl)-methyl, (4-bromobenzenesulfonyl)methyl, (n-butylsulfonyl)methyl, (n-octylsulfonyl)-methyl, 3-(4-methoxybenzenesulfonyl) propyl, (4-methylbenzenesulfonyl)methyl, (benzenesulfonyl)methyl, methyl-3-(1-methylhydantoin), methyl-3-( 1-butylhydantoin) and methyl-3-(5,5-dimethylhydantoin).

9. A compound of claim 1 which is
(1) N-hydroxy 2-[(4-methoxybenzenesulfonyl) methyl]-3-phenyl-propionamide,
(2) N-hydroxy 2-[(benzenesulfonyl)methyl]-3-phenyl-propionamide,
(3) N-hydroxy 2-[(benzenesulfonyl)methyl]-propionamide,
(4) N-hydroxy-2-[(4-methoxybenzenesulfonyl)methyl]-3-(4-methoxybenzenesulfonyl)-propionamide,
(5) N-hydroxy-2-[(4-chlorobenzenesulfonyl)methyl]-3-(4-chlorobenzenesulfonyl)-propionamide,
(6) N-hydroxy-2-[(4-bromobenzenesulfonyl)methyl]-3-(4-bromobenzenesulfonyl)-propionamide,
(7) N-hydroxy-2-[(n-butylsulfonyl)methyl]-3-(n-butylsulfonyl)-propionamide,
(8) N-hydroxy-2-[(n-octylsulfonyl)methyl]-3-(n-octylsulfonyl)-propionamide,
(9) N-hydroxy-2-[(4-methylbenzenesulfonyl)methyl]-3-(4-methylbenzenesulfonyl)-propionamide,
(10) N-hydroxy-2-[(benzenesulfonyl)methyl]-3-(benzenesulfonyl)-propionamide,
(11) N-hydroxy-2-[(4-methoxybenzenesulfonyl)methyl]-5-(4-methoxybenzenesulfonyl)-pentanamide,
(12) N-hydroxy-2-[(n-octylsulfonyl)methyl]-3-(4-methoxybenzenesulfonyl)-propionamide,
(13) N-hydroxy-2-[methyl-3-(1-methylhydantoin)]-3-(4-methoxybenzenesulfonyl)-propionamide,
(14) N-hydroxy-2-[methyl-3-(1-butylhydantoin)]-3-(4-butoxybenzenesulfonyl)-propionamide,
(15) N-hydroxy-2-[methyl-3-(1-butylhydantoin)]-3-(4-methoxybenzenesulfonyl)-propionamide,
(16) N-hydroxy-2-[methyl-3-(5,5-dimethylhydantoin)]-3-(4-methoxybenzene-sulfonyl)-propionamide,
(17) (+)-N-hydroxy-2-[(n-octylsulfonyl)methyl]-3-(4-methoxybenzenesulfonyl)-propionamide,
(18) (−)-N-hydroxy-2-[(n-octylsulfonyl)methyl]-3-(4-methoxybenzenesulfonyl)-propionamide,
(19) (+)-N-hydroxy-2-[methyl-3-(1-methylhydantoin)]-3-(4-methoxybenzenesulfonyl)-propionamide,
(20) (−)-N-hydroxy-2-[methyl-3-(1-methylhydantoin)]-3-(4-methoxybenzenesulfonyl)-propionamide,

(21) (+)-N-hydroxy-2-[methyl-3-(1-butylhydantoin)]-3-(4-butoxybenzenesulfonyl)-propionamide,
(22) (−)-N-hydroxy-2-[methyl-3-(1-butylhydantoin)]-3-(4-butoxybenzenesulfonyl)-propionamide,
(23) (+)-N-hydroxy-2-[methyl-3-(1-butylhydantoin)]-3-(4-methoxybenzenesulfonyl)-propionamide,
(24) (−)-N-hydroxy-2-[methyl-3-(1-butylhydantoin)]-3-(4-methoxybenzenesulfonyl)-propionamide,
(25) (+)-N-hydroxy-2-[methyl-3-(5,5-dimethylhydantoin)]-3-(4-methoxybenzenesulfonyl)-propionamide, or
(26) (−)-N-hydroxy-2-[methyl-3-(5,5-dimethylhydantoin)]-3-(4-methoxybenzenesulfonyl)-propionamide.

10. A compound of claim 1 which is
(1) N-hydroxy-2-[(4-methoxybenzenesulfonyl)methyl]-3-(4-methoxybenzenesulfonyl)-propionamide,
(2) N-hydroxy-2-[(4-chlorobenzenesulfonyl)methyl]-3-(4-chlorobenzenesulfonyl)-propionamide,
(3) N-hydroxy-2-[(4-bromobenzenesulfonyl)methyl]-3-(4-bromobenzenesulfonyl)-propionamide,
(4) N-hydroxy-2-[(n-butylsulfonyl)methyl]-3-(n-butylsulfonyl)-propionamide,
(5) N-hydroxy-2-[(n-octylsulfonyl)methyl]-3-(n-octylsulfonyl)-propionamide,
(6) N-hydroxy-2-[(4-methylbenzenesulfonyl)methyl]-3-(4-methylbenzenesulfonyl)-propionamide,
(7) N-hydroxy-2-[(benzenesulfonyl)methyl]-3-(benzenesulfonyl)-propionamide
(8) N-hydroxy-2-[(4-methoxybenzenesulfonyl)methyl]-5-(4-methoxybenzenesulfonyl)-pentanamide,
(9) N-hydroxy-2-[(n-octylsulfonyl)methyl]-3-(4-methoxybenzenesulfonyl)-propionamide,
(10) N-hydroxy-2-[methyl-3-(1-methylhydantoin)]-3-(4-methoxybenzenesulfonyl)-propionamide,
(11) N-hydroxy-2-[methyl-3-(1-butylhydantoin)]-3-(4-butoxybenzenesulfonyl)-propionamide,
(12) N-hydroxy-2-[methyl-3-(1-butylhydantoin)]-3-(4-methoxybenzenesulfonyl)-propionamide,
(13) N-hydroxy-2-[methyl-3-(5,5-dimethylhydantoin)]-3-(4-methoxybenzenesulfonyl)-propionamide,
(14) (+)-N-hydroxy-2-[(n-octylsulfonyl)methyl]-3-(4-methoxybenzenesulfonyl)-propionamide,
(15) (−)-N-hydroxy-2-[(n-octylsulfonyl)methyl]-3-(4-methoxybenzenesulfonyl)-propionamide,
(16) (+)-N-hydroxy-2-[methyl-3-(1-methylhydantoin)]-3-(4-methoxybenzenesulfonyl)-propionamide,
(17) (−)-N-hydroxy-2-[methyl-3-(1-methylhydantoin)]-3-(4-methoxybenzenesulfonyl)-propionamide,
(18) (+)-N-hydroxy-2-[methyl-3-(1-butylhydantoin)]-3-(4-butoxybenzenesulfonyl)-propionamide,
(19) (−)-N-hydroxy-2-[methyl-3-(1-butylhydantoin)]-3-(4-butoxybenzenesulfonyl)-propionamide,
(20) (+)-N-hydroxy-2-[methyl-3-(1-butylhydantoin)]-3-(4-methoxybenzenesulfonyl)-propionamide,
(21) (−)-N-hydroxy-2-[methyl-3-(1-butylhydantoin)]-3-(4-methoxybenzenesulfonyl)-propionamide,
(22) (+)-N-hydroxy-2-[methyl-3-(5,5-dimethylhydantoin)]-3-(4-methoxybenzenesulfonyl)-propionamide, or
(23) (−)-N-hydroxy-2-[methyl-3-(5,5-dimethylhydantoin)]-3-(4-methoxybenzenesulfonyl)-propionamide.

11. A method of inhibiting excess matrix metalloproteinase which comprises administering to a patient in need thereof an effective amount of a compound of claim 1.

12. The method of claim 11 wherein matrix metalloproteinases comprises stromelysin, collagenase, and gelatinase.

13. A method of treating a human suffering from or susceptible to diseases involving connective tissue degradation which comprises administering to a patient in need thereof an effective amount of a compound of claim 1.

14. The method of claim 13 wherein the diseases related to connective tissue degradation are osteoarthrits, rheumatoid arthritis, septic arthritis, osteopenias, steoporosis, tumor metastasis, periodontitis, gingivitis, corneal epidermal ulceration, or gastric ulceration.

15. The method of claim 11 wherein the effective amount of the compound of claim 1 is administered orally, parenterally, or topically in a pharmaceutical composition.

16. The method of claim 13 wherein the effective amount of the compound of claim 1 is administered orally, parenterally, or topically in a pharmaceutical composition.

17. The method of claim 11 or 13 wherein said compound is administered in an amount of from about 0.1 to about 100 mg/kg of body weight/day.

18. A pharmaceutical composition which comprises an amount of the compound of claim 1 effective to inhibit excess matrix metalloproteinase and a pharmaceutically acceptable carrier.

* * * * *